United States Patent [19]

Dennis

[11] Patent Number: 5,569,595
[45] Date of Patent: Oct. 29, 1996

[54] PRODUCTION OF POLY-β-HYDROXYBUTYRATE IN PROKARYOTIC HOST CELLS

[75] Inventor: Douglas E. Dennis, Weyers Cave, Va.

[73] Assignee: Center for Innovative Technology, Herndon, Va.

[21] Appl. No.: 35,433

[22] Filed: Mar. 24, 1993

Related U.S. Application Data

[63] Continuation-in-part of Ser. No. 890,925, May 29, 1992, and Ser. No. 767,008, Sep. 27, 1991, Pat. No. 5,371,002.

[51] Int. Cl.$^6$ .............................. C12P 7/62; C12N 15/00; C12N 1/20
[52] U.S. Cl. .................. 435/135; 435/172.3; 435/252.3; 435/252.33; 435/252.4; 935/60
[58] Field of Search ................................ 435/135, 172.3, 435/252.3, 252.33, 252.4

[56] References Cited

U.S. PATENT DOCUMENTS 4,806,480  2/1989  Lopez ................................... 435/320.1
5,245,023  9/1993  Peoples et al. .......................... 435/135

OTHER PUBLICATIONS

Slater et al., Appl. Env. Microbiol. 58(4) : 1089–1094 (Apr. 1992).

Slater et al., J. Bact. 170(10) : 4431–4436 (Oct. 1988).

*Primary Examiner*—Stephanie W. Zitomer
*Attorney, Agent, or Firm*—Seed and Berry LLP

[57] ABSTRACT

The present invention provides methods for the production of poly-β-hydroxybutyrate, comprising the steps of (a) introducing into a prokaryotic host cell capable of metabolizing sucrose a vector construct which directs the expression of a sequence which encodes a poly-β-hydroxybutyrate biosynthetic pathway, (b) culturing the host cell in medium containing sucrose, and (c) isolating poly-β-hydroxybutyrate from the cultured host cell.

17 Claims, 18 Drawing Sheets

PRODUCTION OF POLY-β-HYDROXYBUTYRATE IN PROKARYOTIC HOST CELLS

CROSS REFERENCE TO RELATED APPLICATIONS

This application is a continuation-in-part of application U.S. Ser. No. 07/890,925, filed May 29, 1992, and a continuation-in-part of Ser. No. 07/767,008 filed Sep. 27, 1991, U.S. Pat. No. 5,371,002, issued Dec. 6, 1994, both of which are expressly incorporated by reference herein.

TECHNICAL FIELD

The present invention relates generally to the production of polymers in prokaryotic host cells, and more specifically, to the production of poly-β-hydroxyalkanoates such as poly-β-hydroxybutyrate, in prokaryotic host cells capable of metabolizing sucrose.

BACKGROUND OF THE INVENTION

Poly-β-hydroxybutyrate "PHB" is a naturally occurring bacterial polyester that was discovered by Lemoigne in 1926 (Lemoigne, *Bull. Soc. Chim. Biol.* 8:770, 1926). PHB is believed to exist as a bacterial energy storage compound which is accumulated during times of nutritional stress, and is degraded when the stress is relieved (Oeding et al., *Biochemical Journal* 134:239–248, 1973; Senior et al., *Biochemistry Journal* 134:225–238, 1973). The most remarkable aspect of PHB accumulation is the intracellular levels to which it can accumulate. In *Alcaligenes eutrophus*, PHB levels have been known to reach 80% of the cell dry weight (Oeding et al., *Biochemical Journal* 134:239–248, 1973).

In the early 1950's it was discovered that purified PHB was, in fact, a biodegradable thermoplastic that could be molded or shaped into a variety of items. Its biodegradability is derived from the fact that many bacteria that have the biosynthetic portion of the pathway also contain a biodegradative pathway (Anderson et at., *Microbiological Reviews* 54(4):450–472, 1990). Theoretically, thermoplastic items made from PHB could then be composted in landfills, where they can be degraded by both aerobic and anaerobic bacteria (Winton, *Chemical Week*, 55–57, Aug. 28, 1985). Commercialization efforts were initiated by W. R. Grace, but were halted when it became apparent that there were formidable technical difficulties to be overcome, and public interest in the project was low (Holmes, *Phys. Technology* 16:32, 1985).

PHB research languished until the 1970's, when the laboratories of H. G. Schlegel in Germany and E. A. Dawes in England undertook to elucidate the enzymological mechanism of PHB production. In a series of publications, both laboratories defined the pathway of PHB biosynthesis in Alcaligenes and Azotobacter, (Anderson et al., *Microbiological Reviews* 54(4):450–472, 1990; Jackson et al., *Journal of General Microbiology* 97:303–313, 1976; Oeding et al., *Biochemical Journal* 134:239–248, 1973; Ritchie, *Biochemistry Journal* 121:309–316, 1972; Schlegal et al., *Antonie Van Leeuwenhoek* 32:277, 1966; Senior et al, *Biochemistry Journal* 134:225–238, 1973; Ward et al., *Journal of General Microbiology* 102:61–68, 1977).

In the early 1980's interest in PHB was again stimulated when it was found that PHB is actually part of a family of polyesters, termed poly-β-hydroxyalkanoates (PHAs) (Findlay et al., *Applied and Environmental Microbiology* 45(1):71–78, 1983). Loosely defined, PHAs are a family of polymerized fatty acid esters, in which the fatty acid monomer is normally from 4–10 carbons. PHAs that contain higher carbon-number fatty acids can be made into a more flexible thermoplastic, whereas PHAs containing lower carbon-number fatty acids tend to be more brittle (Byrom, *Trends Biotechnology* 5:246–250, 1987). For example, poly-(3-hydroxybutyrate-co-3-hydroxyvalerate) is much more amenable to plastic film production than poly-3-hydroxybutyrate, which is a brittle plastic.

The environmental and commercial importance of PHAs lies in their potential to reduce the volume of solid waste. Although estimates vary widely, the best data available indicates that 7–10% of all landfill waste is plastic (Beardsley et al., *Scientific American*, 1988). This is the equivalent of millions of pounds of plastic disposed in this manner every day. Since the average life of such plastic can be as long as several hundred years, poly-β-hydroxalkanoates offer distinct environmental advantages (e.g., a 0.07 mm-thick film of PHB degrades in 10 weeks in soil; Doi et al, *Applied and Environmental Microbiology* 55(11):2932–2938, 1989).

Unfortunately, PHA technology has not yet replaced petrochemical-based plastics because of the high cost of production. Currently, PHAs are being marketed for approximately $14 per pound, whereas petroleum-based plastics sell for less than $1 per pound (Winton, *Chemical Week*, 55–57, Aug. 28, 1985). The primary reason for the high cost of poly-β-hydroxyalkanoates is the mode of production: fermentation times are as long as 100 hours, final PHA levels fluctuate, purification procedures are cumbersome and expensive, and substrate costs are inordinately high (Byrom et al., *Trends Biotechnology* 5:246–250, 1987). Therefore, before these plastics can find their way to the commodity marketplace, significant improvements are necessary.

The present invention overcomes previous difficulties of PHA production, and further provides other, related advantages.

SUMMARY OF THE INVENTION

The present invention provides methods for the production of poly-β-hydroxybutyrate, as well as poly-β-hydroxyalkanoate copolymers. Briefly, within one aspect of the present invention methods for the production of poly-β-hydroxybutyrate are provided, comprising the steps of (a) introducing into a prokaryotic host cell capable of metabolizing sucrose, a vector construct which directs the expression of a sequence which encodes a poly-β-hydroxybutyrate biosynthetic pathway, (b) culturing the host cell in medium containing sucrose, and (c) isolating poly-β-hydroxybutyrate from the cultured host cell.

Within another aspect of the present invention, methods for the production of poly-β-hydroxyalkanoate copolymer is provided, comprising the steps of (a) introducing into a prokaryotic host cell capable of metabolizing sucrose and expressing acetate utilization enzymes constitutively, a vector construct which directs the expression of a sequence which encodes a poly-β-hydroxybutyrate biosynthetic pathway, (b) culturing the host cell in medium containing propionate or a derivative thereof, and sucrose, and (c) isolating the poly-β-hydroxyalkanoate copolymer from the cultured host cell.

Within another aspect of the invention, Enterobacteriaceae are provided which are capable of metabolizing sucrose, and which contain a vector construct that directs the expression of a sequence which encodes a biosynthetic pathway of poly-β-hydroxybutyrate.

Within preferred embodiments of the invention, the prokaryotic host cell is an Enterobacteriaceae. Particularly preferred Enterobacteriaceae include *E. coli* and Klebsiella, including for example *Klebsiella aerogenes*. Within other embodiments of the invention, the medium contains sucrose as the principal carbon source. In addition, within particularly preferred embodiments of the above-described methods, the medium comprises or even merely consists of molasses.

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety.

DETAILED DESCRIPTION OF THE INVENTION

Figure 1:
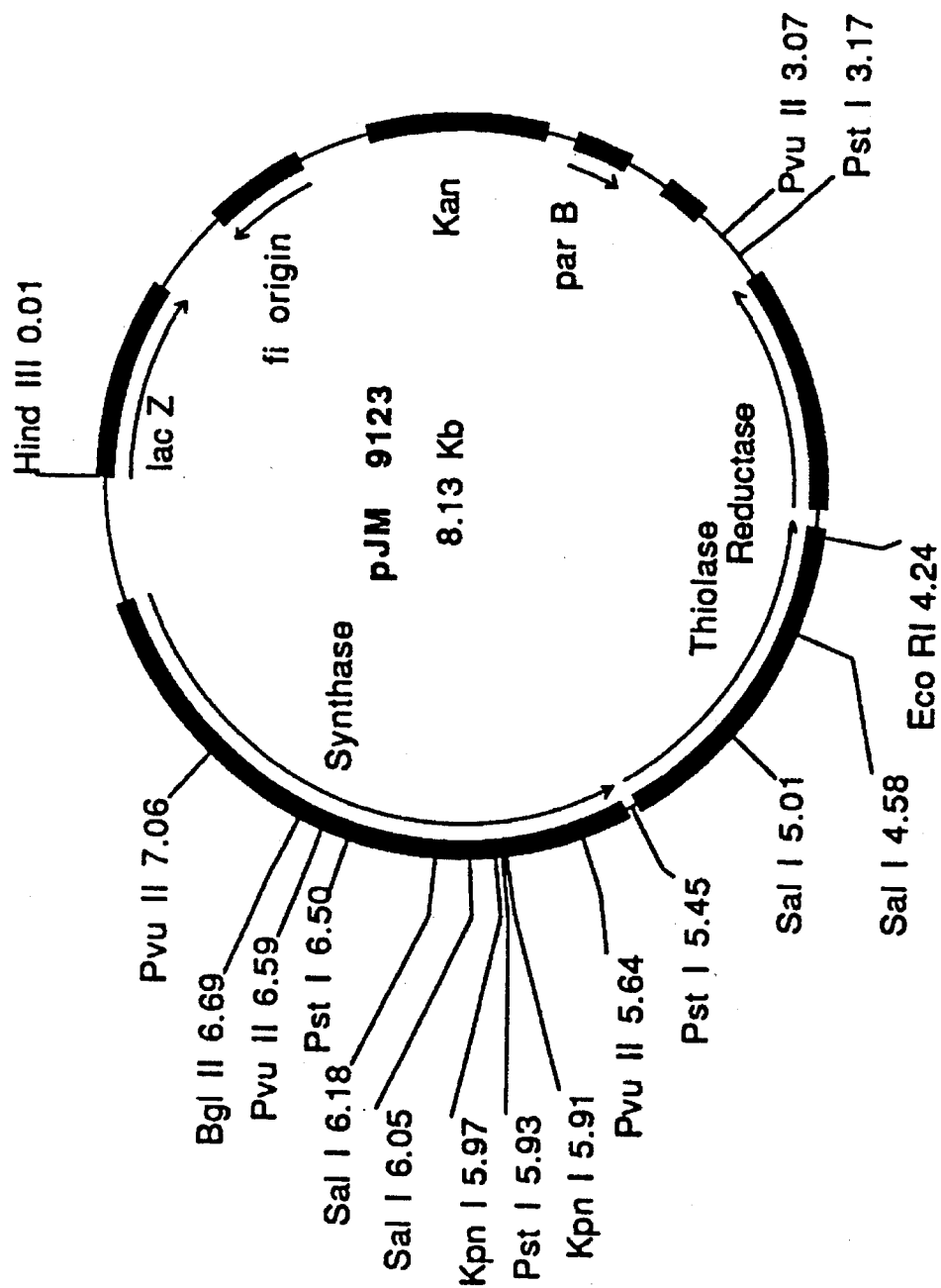
FIG. 1 is a plasmid map of pJM9123.

As noted above, the present invention provides methods for the production of poly-β-hydroxybutyrate, as well as poly-β-hydroxyalkanoate copolymers. Within one aspect of the present invention, methods for the production of poly-β-hydroxybutyrate are provided comprising the steps of (a) introducing into a prokaryotic host cell capable of metabolizing sucrose a vector construct which directs the expression of a sequence which encodes a poly-β-hydroxybutyrate biosynthetic pathway, (b) culturing the host cell in medium containing sucrose, and (c) isolating poly-β-hydroxybutyrate from the cultured host cell.

Various prokaryotic host cells may be utilized within the context of the present invention. Generally, preferred prokaryotic host cells should have a well-characterized genetic system, including known cloning vectors and methods of genetic manipulation. They should also preferably grow well in minimal medium, ideally to a high cell density, and without any special requirements (physical or physiological). In addition, as noted above the host cell is capable of metabolizing sucrose. Representative examples of such host cells include members of the Bacillaceae, Nocardiaceae, Streptomycetaceae, Pseudomonadaceae, Corynebacteria, and Enterobacteriaceae. Members which are capable of metabolizing sucrose may readily be identified based upon their known growth requirements, or, if unknown, by determining whether the bacteria grows on medium containing sucrose as the sole source of carbon.

Preferred host cells in the Family Enterobacteriaceae include Escherichia, Citrobacter, Klebsiella, Enterobacter, and Serratia, as well as Zymomonas and Flavobacterium, which are within the Enterobacteriaceae but of uncertain affiliation. Particularly preferred host cells include *E. coli, Klebsiella oxytoca,* and *Klebsiella aerogenes*. Preferred host cells in the Family Pseudomonaceae include *P. fluorescens*, which is able to utilize sucrose.

The above-described prokaryotes may be readily obtained from a variety of commercial sources including, for example, the American Type Culture Collection (ATCC) (Rockville, Md.). Alternatively, many of the above-described bacteria may be isolated from sources which are known by those of skill in the art to contain such prokaryotes, based upon techniques which are known in the art (see Bergy's *Shorter Manual of Determinative Bacteriology*, Williams & Wilkins (pub.), John G. Holt (ed.), 8th edition, 1977).

Once a prokaryotic host cell capable of metabolizing sucrose has been obtained, a vector construct which directs the expression of a sequence which encodes a poly-β-hydroxybutyrate biosynthetic pathway is introduced into the host cell. Within the context of the present invention, a vector construct is understood to refer to an assembly which is capable of expressing the sequence(s) of interest. The vector construct must include an origin of replication, and preferably includes a stabilization locus (e.g., the parB locus), and selectable antibiotic resistance markers such as chloramphenicol, kanamycin, or tetracycline resistance genes. In addition, the vector construct may also contain a genetic system that allows control of copy number (e.g., RAPT from Nycomed), a regulatable promoter, as well as a translation termination sequence, and one or more restriction sites.

As noted above, the vector construct is utilized to introduce a sequence which encodes a poly-β-hydroxybutyrate biosynthetic pathway into the host cell. The three step biosynthetic pathway for poly-β-hydroxybutyrate has been found in many prokaryotic organisms, including Azotobacter, Beigerinckia, Alcaligenes, Pseudomonas, Rhizobium, and Rhodospidllum, and has been studied extensively in *A. eutrophus* and *Azotobacter beijerinckii*. Briefly, β-ketothiolase first catalyzes the reversible condensation of two acetyl coenzyme A (CoA) molecules to acetoacetyl-CoA. The acetoacetyl-CoA is then reduced by acetoacetyl-CoA reductase to D-(-)3 hydroxybutyryl-CoA. Enzyme action of the acetoacetyl-CoA reductase is dependent on NADPH. PHB synthetase polymerizes the D-(-)-3-hydroxybutyryl-CoA to poly-β-hydroxybutyrate.

The poly-β-hydroxybutyrate biosynthetic pathway was first cloned from *A. eutrohpus* into *E. coli* (see Slater et al., *J. Biol.* 170:4431, 1988; see also U.S. Ser. No. 07/528,549, filed Jun. 7, 1989, and U.S. Ser. No. 07/705,806, filed May 24, 1991, all of which are expressly incorporated herein by reference). The cloning of the PHB biosynthetic pathway into *E. coli* has also been later described by Schubert et al., *J. Bacter.* 170:5837, 1988; Peoples, et al., *J. Biol. Chem.* 264:15298, 1989; and Peoples et al., *J. Biol. Chem.* 264:15293, 1989.

Figure 2:
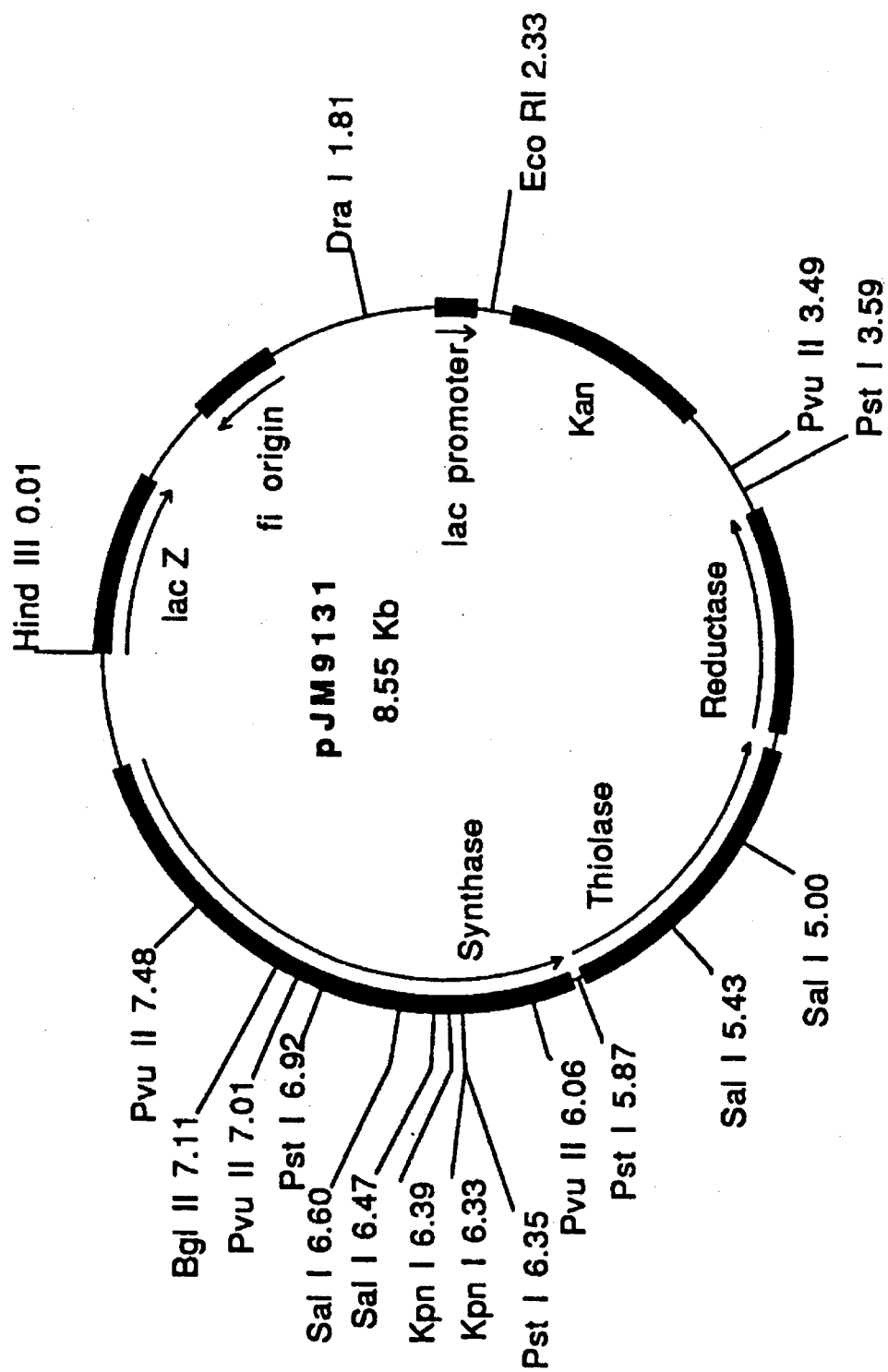
FIG. 2 is a plasmid map of pJM9131.
Figure 3:
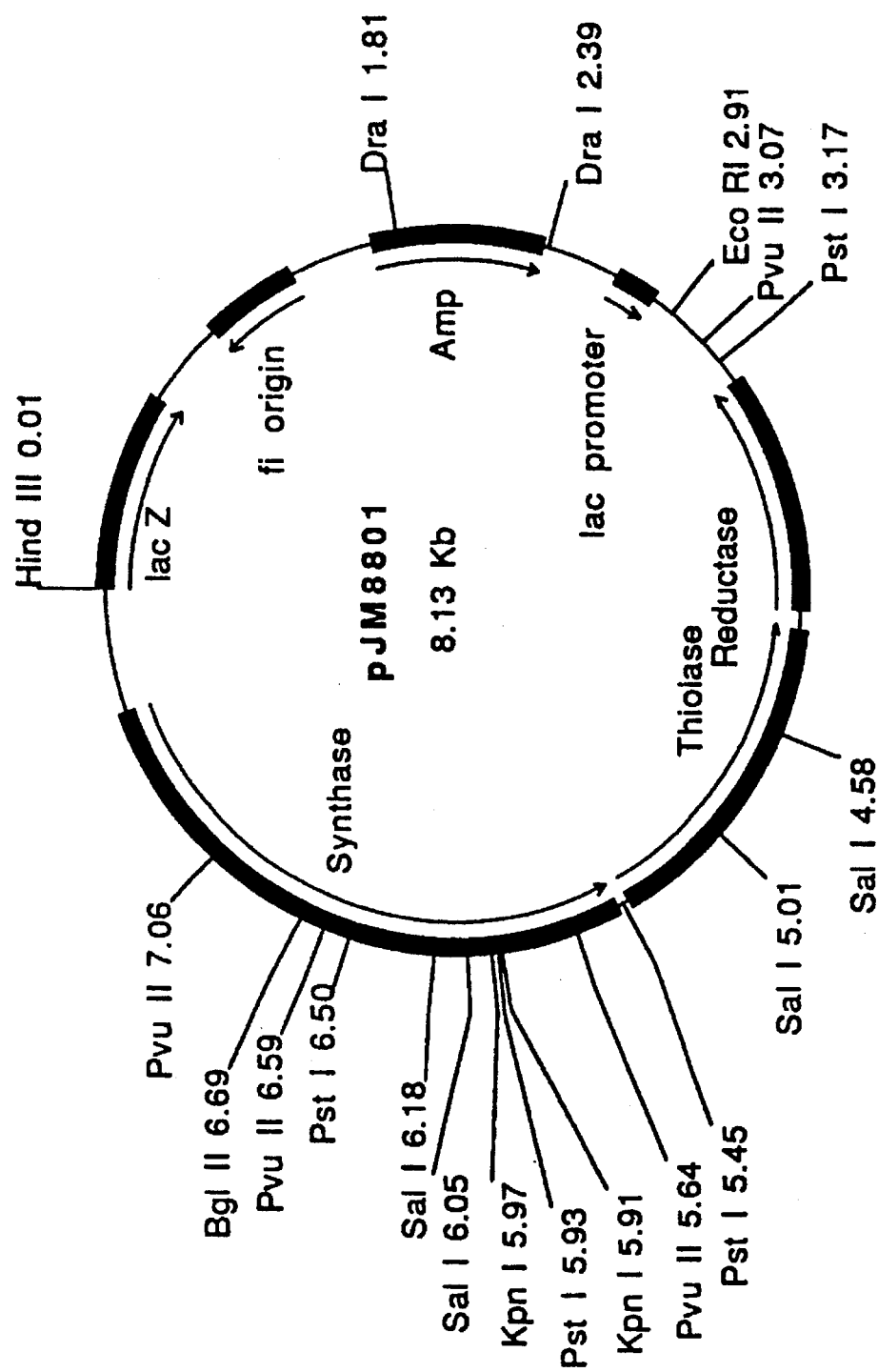
FIG. 3 is a plasmid map of pJM8801.
Figure 18:
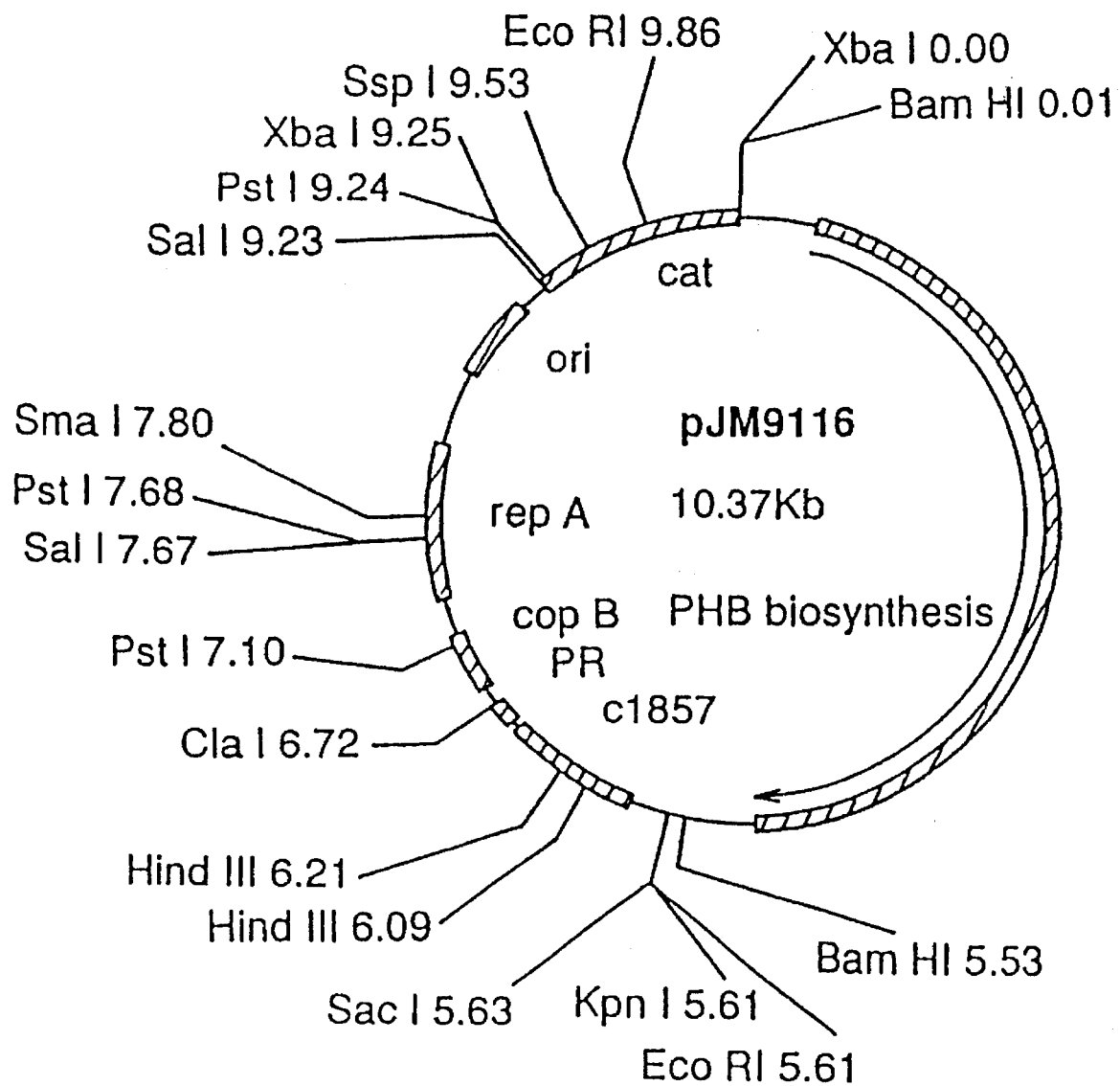
FIG. 18 is a plasmid map of pJM9116.

Particularly preferred vector constructs which direct the expression of the poly-β-hydroxybutyrate biosynthetic pathway, and which may be utilized within the present invention include pJM8801 (formerly p4A, ATCC Deposit No. 68329; see also FIG. 3), pJM9116 (ATCC Deposit No. 68992; see also FIG. 18), pJM9123 (see FIG. 1) and pJM9131 (see FIG. 2). pJM9123 may be constructed essentially as described by Slater et al. in *Appl. and Env. Micro.* 58(4):1089–1094, 1992. Briefly, pJM9123 was constructed by digesting pJM8801 with restriction endonucleases Dra I and EcoR I. The resulting 6.5 kb fragment carrying the PHB operon and plasmid origin of replication was rendered blunt-ended by using Klenow polymerase with the appropriate reaction conditions. The blunt-ended fragment was subsequently ligated to a 1.6 kb fragment obtained from plasmid pKG1022 by digestion with the restriction endonuclease HincII. This fragment contains the kanamycin resistance gene and the ParB locus (Gerdes, *Bio/Technology* 6:1402–1405, 1988).

Similarly, pJM9131 was constructed by cutting pJM8801 with EcoR I, adding a kanamycin-resistance marker with EcoR I ends (GENBLOCK™, Pharmacia), and religating at EcoR I. Next, the gene for ampicillin resistance was removed by digestion with Dra I, and the plasmid religated. The resulting multi-copy plasmid confered kanamycin resistance, but not ampicillin resistance.

A variety of other vector constructs which are described in co-pending applications U.S. Ser. Nos. 07/890,925 and 07/528,549, (which are expressly incorporated by reference herein) may also be utilized within the context of the present invention. Examples include pJM9101 (ATCC Deposit No. 69000), pJM9113 (ATCC Deposit No. 68989), pJM9114 (ATCC Deposit No. 68990), pJM9115 (ATCC Deposit No. 68991), pJM9117 (ATCC Deposit No. 68993), pJM9118 (ATCC Deposit No. 68994), pJM9119 (ATCC Deposit No. 68995), pJM9120 (ATCC Deposit No. 68996), pJM9125 (ATCC Deposit No. 68998), and pJM9126 (ATCC Deposit No. 68999).

The host cell is then cultured in medium containing sucrose, preferably as the principal carbon source. A variety of types of sucrose may be utilized within the context of the present invention, including for example, molasses obtained from sugar cane or beets, which contains unrefined sucrose, or purified sucrose. Preferred conditions for culture of the host cell will vary with the host and the vector construct selected. For example, *E. coli* is normally grown at 37° C., in an orbital incubator (225 rpm). However, with some vectors, it may be grown at 30° C. to keep the vector uninduced, and at 34° to 38° C. to induce the vector. Preferably, the host cell is grown on minimal media (e.g., M9 minimal media), and is grown past the log phase and into the stationary phase of bacterial growth.

Once the host cell has been cultured under conditions and for a time sufficient to generate poly-β-hydroxybutyrate, the poly-β-hydroxybutyrate is isolated from the host cell. Isolation may be accomplished by a variety of methods. For example, the host cells may be lysed, and PHB agglomerated essentially as described in U.S. Ser. Number 07/528, 549, which is hereby incorporated by reference in its entirety. Alternatively, lysozyme plasmids may be introduced into the host cell, and thereby utilized to enhance isolation of PHB. Such methods are described in detail in U.S. Ser. Number 07/890,925, filed May 29, 1991, which is hereby incorporated by reference in its entirety.

Within a preferred embodiment, after the host cells have reached the stationary phase of growth, they are washed once with water to remove debris. The cells are then heat sterilized, and while still hot, SDS (approximately 0.1%) and EDTA (approximately 2 mM) are added, and the mixture is stirred for about one hour at a temperature of 60° C. to 80° C. During this time, the cells will lyse, releasing the PHB granules. The granules are separated from cell debris by centrifugation, and then washed twice with water.

Through use of the above-described techniques, PHB may be isolated to approximately 98% or 99% purity, as determined by gas chromatography. Briefly, PHB purity may be calculated by determining the area under the PHB peak, and dividing it by the areas under all peaks in the chromatogram.

Within another aspect of the present invention, methods for the production of poly-β-hydroxyalkanoate copolymer are provided, comprising the steps of (a) introducing into a prokaryotic host cell capable of metabolizing sucrose and expressing acetate utilization enzymes constitutively, a vector construct which directs the expression of a sequence which encodes a poly-β-hydroxybutyrate biosynthetic pathway, (b) culturing the host cell in medium containing propionate or a derivative thereof, and sucrose, and (c) isolating the poly-β-hydroxyalkanoate copolymer from the cultured host cell. Suitable host cells, vector constructs, as well as methods for culturing and isolating PHB from such host cells, for use within this aspect of the present invention, have been described above.

Briefly, as noted above, poly-β-hydroxyalkanoates (PHA's) are a heterogeneous family of biodegradable aliphatic polyesters which include, for example, derived polymers such as poly-β-hydroxybutyrate (PHB) and poly-β-hydroxyvalerate (PHV). The PHA copolymers produced according to the present invention can be "random" copolymers, wherein the PHA copolymer comprises PHB and PHV dispersed randomly in the polymer backbone, or as "semi-random" or blocked copolymers, wherein the PHA copolymer comprises long or short chains of one particular PHA, for example PHB, which is separated by long or short chains of other PHAs, for example, randomly dispersed PHB and PHV.

The present invention provides for the production of PHA's by introducing a vector construct which directs the expression of a sequence which encodes a poly-β-hydroxybutyrate biosynthetic pathway, into a host cell which expresses acetate utilization enzymes. Within one embodiment of the invention, the host cell may express acetate utilization enzymes after induction of these enzymes by growth on a first substrate, which induces production of such genes in the host. Representative examples of such substrates include acetate and propionate, or derivatives and combinations thereof. Briefly, as will be understood by one of ordinary skill in the art, a variety of propionates (wherein propionates are represented by —$\beta C$—$\alpha C$—$CO_2 X$; and X is either a cationic metal or alkyl group) may be utilized within the present invention. Examples include either monosubstituted or disubstituted propionates wherein the substituent groups may be selected from halogens (e.g., fluorine, chlorine, bromine, and iodine), oxygen (alcohols and their derivatives, including O—N, O—S, and O—P compounds), sulfur (thiols and their derivatives, including S—O compounds), and phosphorous (including phosphines, phosphites and phosphates).

Thereafter, the host is cultured on a second substrate comprising propionate or derivatives thereof, and sucrose, during which time the host expresses the PHB biosynthetic pathway, and produces a PHA copolymer.

Within another embodiment, PHA copolymers may be produced by introducing a vector construct which directs the expression of a sequence for the PHB biosynthetic pathway into a host cell which expresses acetate utilization enzymes constitutively. The resulting recombinant host may then be cultured in a substrate comprising sucrose and propionate or derivatives thereof.

A variety of methods may be utilized to ensure that the host cell expresses acetate utilization enzymes constitutively. For example, within one embodiment, a mutant fadR gene (DeRusso and Nunn, *J. of Bact.* 161(2):583–588, 1985) and/or a mutant atoC gene (Jenkins and Nunn, *J. of Bact.* 169(5):2096–2012, 1987) is transduced into the host cell. Both of these mutations may act to increase the uptake of propionate (and hence, increase PHV production), albeit by different mechanisms. Briefly, atoC is a positive regulator which can be mutated to be constitutively expressed, and therefore, utilized to increase the uptake of priopionate, as well as other fatty acids. In contrast to atoC, fadR is a repressor of fatty acid degradative genes, and therefore represses the transcription of fatty acid degradative enzymes. Mutation of this gene results in the induction and transcription of these enzymes, which works to increase the amount of propionate and propionyl Co-A in the cell. Therefore, introduction of either the atoC or the fadR mutations into the host cell will serve to cause constitutive expression of acetate utilization genes. A representative example is set forth below in Examples 13, 14 and 15.

Alternatively, within another embodiment of the invention, acetate kinase and phosphotransacetylase synthetase genes can be cloned into a vector construct which directs its expression. Briefly, these genes are able to utilize propionate as a substrate, and change it to propionyl-CoA. Propionyl-CoA is then incorporated directly into PHB-co-V starting with the PHB biosynthetic enzyme beta-ketothiolase. The first enzyme of the PHB pathway, beta-ketothiolase, has a substrate specificity that allows it to act on propionyl-CoA as well as acetyl-CoA (Haywood et al., *FEMS Microbiol. Letters* 52:91, 1988). Therefore, propionyl-CoA and acetyl-CoA are condensed to acetopropionyl-CoA, which is then reduced to beta-hydroxyvaleryl CoA, which is subsequently polymerized into the PHB/PHV copolymer.

Within one embodiment of the invention, low molecular weight polymers (e.g., less than $1 \times 10^5$ Daltons) are produced. In order to increase the molecular weight of polymers produced by the methods described herein, a variety of methods may be utilized. For example, if the presence of a depolymerase or its gene were detected, the function of this gene could be deleted by crossing over with a mutant depolymerase. Alternatively, a variety of experimental parameters may be modified in order to vary the molecular weight of the resultant polymer. Examples of such parameters include pH, growth temperature, ammonium concentration, carbon source, and differential levels of the synthase, thiolase, and reductase.

The following examples are offered by way of illustration, and not by way of limitation.

EXAMPLES

EXAMPLE 1

Isolation of a Sucrose-Utilizing Bacterium

A 50 ml sample of water was taken from Black's Run in Harrisonburg, Va. This sample was diluted 1:10 and 1:100 with sterile saline (0.85%), and 1 ml was plated into Mac-Conkey's agar (Baxter Scientific Products) containing 0.4% sucrose (GenAR grade; Mallinckrodt Chemicals). The plates were incubated overnight at 37° C. aerobically, after which 30 red colonies were selected and streaked onto mfc Endo agar plates. The plates were incubated at 37° C. aerobically. The next day approximately 23 metallic green colonies (presumptively Enterobacteriaceae such as *E. coli*) were selected and stabbed into Simmons Citrate tubes (Baxter Scientific Products). Two isolates gave a negative reaction on Simmons Citrate, and thus were identified as *E. coli*.

Upon further characterization, these isolates were found to be Gram-negative (standard Gram stain), rod-shaped (by microscopic examination), facultative anaerobes (by their ability to grow in stab culture at the bottom of the tube), sucrose positive (from MacConkey plates), and coliforms (by metallic sheen on mfc Endo broth).

Four of the above cloned isolates, #14, #21, #3, and #11 were streaked for isolation, and then subjected to biochemical characterization using the Enterotube II system from Roche Diagnostic Systems. A laboratory strain of *E. coli* was utilized as the positive control. Isolates # 14 and #21 gave results which were essentially the same as the positive control, but #21 gave slightly stronger results. Results for isolate #21 are set forth below:

| Test | Result |
| --- | --- |
| Glucose fermentation | positive |
| Gas production from glucose | variable |
| Lysine utilization | positive |
| Ornithine utilization | positive |
| Hydrogen sulfide production | negative |
| Indole production | positive |
| Adonnitol utilization | negative |
| Lactose utilization | positive |
| Arabinose utilization | positive |
| Sorbitol utilization | positive |
| Voges/Proskauer test | negative |
| Dulcitol utilization | negative |
| Phenalanine deaminase produced | negative |
| Urea hydrolyzed | negative |
| Citrate utilization | negative |

Based upon these tests, isolate #21 was presumptively identified as *E. coli*.

Isolate #21 was also tested for antibiotic resistance since it is generally believed that the "sucrose" gene is carried by the same plasmid which carries the tetracycline-resistance gene, pUR400. Briefly, isolate #21 was plated on agar plates containing specific antibiotics, and analyzed for growth. Antibiotic levels in the agar plates were: Ampicillin—20

μg/ml, chloramphenicol—20 μg/ml, tetracycline—10 μg/ml, and kanamycin—10 μg/ml. The isolate was found to be resistant to tetracycline, but not kanamycin or chloramphenicol. It was variably resistant to ampicillin.

To confirm that isolate #21 was, indeed, an *E. coli*, it was further characterized by its fatty acid profile. Based upon this profile, isolate #21 was confirmed to be an *E. coli* of subgroup A. This isolate was designated JMU 213.

EXAMPLE 2

Insertion of PHB-Biosynthesis Genes into JMU 213

Plasmids pJM9123 (FIG. 1) and pJM9131 (FIG. 2) were each electroporated into JMU 213 essentially as described below. These plasmids contain the PHB-encoding genes and a kanamycin selectable marker. pJM9123 differs slightly from pJM913 1 in that it has the parB gene.

A. Electroporation

Electroporation is accomplished essentially as follows. Briefly, a 3 ml tube culture of Luria Broth ("LB") was inoculated with JMU 213, and grown overnight on an orbital incubator (225 rpm) at 37° C. The next morning, 1 ml of the saturated culture was inoculated in 50 ml of LB in a baffled 250 ml flask, and the culture was grown as above until the optical density at 600 nm reached approximately 0.5. At this time, the culture was placed on ice for 10 minutes. It was then transferred into a sterile 50 ml capped, conical-ended, plastic tube (Baxter Scientific), and centrifuged at 2,000 g for 10 minutes. The supernatant was aseptically removed and 40 ml of sterile ice-cold deionized water was added to the pellet. The pellet was resuspended by vortexing, followed by pelleting as described above. The supernatant was again aseptically aspirated, after which the pellet was again resuspended with 40 ml of sterile ice-cold, deionized water. The bacteria were again pelleted by centrifugation, and the supernatant was aseptically aspirated. Forty ml of sterile ice-cold water was added a final time, the pellet was resuspended, and a final pellet was obtained by centrifugation as above. The supernatant was again aseptically aspirated and the pellet was resuspended in a final volume of approximately 0.2 ml. One hundred microliters of this suspension was removed to a chilled microcentrifuge tube, and 1 μl of plasmid DNA (pJM9123 or pJM913 1) was added and mixed. This mixture was added to an electroporation cuvette (BioRad Laboratories), and subjected to a pulse of 2.5 kV at 200 mOhms, and 25 μfarads (Gene Pulser Apparatus, BioRad Laboratories). The cuvette was removed and the bacterial suspension transferred to a 3 ml culture of LB in a sterile 16×100 mm tube. The tube was incubated for 1 hour on an orbital shaker incubator at 37° C., 225 rpm. Aliquots of 100 μl, 10 μl or 1 μl were spread onto Luria agar plates containing 50 μl/ml kanamycin, and incubated at 37° C. in a convection incubator for 1 day. Isolated colonies were then selected and tested for their ability to synthesize PHB when grown in M9 minimal medium containing 1% glucose.

Many electroporatants were found that produced PHB. One isolate was selected, and designated JMU 213 (pJM9123).

EXAMPLE 3

PHB Production in *E. coli*

A. PHB production in *E. coli* grown in sucrose-containing medium

Three flasks containing 50 ml of M9 minimal medium, kanamycin (100 μl/ml) (to stabilize the PHB plasmid), and tetracycline (50 μl/ml) (to stabilize the sucrose-utilization plasmid) were prepared. Sucrose was added to each of these flasks to a final concentration of 1% (#1), 0.5% (#2), or 0.1% (#3).

An overnight culture of JMU 213 (pJM9123) was prepared by inoculating an isolated colony from a Luria agar plate (100 μl/ml kanamycin) into 3 ml tube of LB, and incubating in an orbital shaker (225 rpm) at 37° C. In the morning, 1 ml of JMU 213 (pJM9123) from these overnight cultures was inoculated into each of the above-described flasks. The 50 ml cultures were grown in 250 ml shake flasks overnight at 37° C. on an orbital shaker (225 rpm). After approximately 24 hours of growth, samples were taken and analyzed by methanolysis (see Example 4B, below).

| Flask | PHB Production |
|---|---|
| 1 (1% sucrose) | 1.29 mg/ml PHB |
| 2 (0.5% sucrose) | 0.2 mg/ml |
| 3 (0.1% sucrose) | negligible PHB |

From these results it can be seen that PHB can be made in *E. coli* which utilizes sucrose as the carbon source.

B. PHB production in *E. coli* grown in molasses

Six flasks of M9 minimal media were prepared containing kanamycin (100 μg/ml), and high-test molasses. The six flasks had varying amounts of high-test molasses: 1, 2, 3, 4, 5, and 6%. JMU 213 (pJM9123) was grown from an isolated colony on a Luria agar plate (100 μg/ml kanamycin) in several 3 ml tubes of LB containing 100 μg/ml kanamycin overnight in an orbital shaker (225 rpm) at 37° C. In the morning, 1 ml of this culture was inoculated into each of the 50 ml cultures in 250 ml shake flasks described above, and grown at 37° C. in a rotary shaker incubator (225 rpm) for approximately 24 hours. The PHB concentration in each flask was then measured by methanolysis, as described in Example 4B.

| Percentage Molasses | PHB Concentration |
|---|---|
| 1% high test | 0.71 mg/ml |
| 2% high test | 1.86 mg/ml |
| 3% high test | 2.77 mg/ml |
| 4% high test | 2.9 mg/ml |
| 5% high test | 2.7 mg/ml |
| 6% high test | 2.23 mg/ml |

From this data, it has been determined that PHB can be made by JMU 213 (pJM9123) when the bacteria is grown in medium containing molasses, and that the apparent optimum concentration of molasses is between 3 and 4%.

EXAMPLE 4

Comparison of PHB Production From Sucrose and Glucose for *E. coli* JMU 213

A. Sample Preparation

JMU 213 (pJM9131) was inoculated into a 250 ml shake-flask containing 50 ml of LB and 50 μg/ml kanamycin, and grown overnight in an orbital shaker at 37° C. One milliliter of this culture was inoculated into eight 250 ml sterilized, baffled Erlenmeyer culture flasks, each containing 50 ml of M9 minimal medium, kanamycin (50 μg/ml), and 1%, 2%, 3%, 4%, or 5% (w/v) of either sucrose or glucose. Samples were analyzed by methanolysis as described below.

B. Methanolysis

Each flask was incubated overnight at 37° C. in an orbital shaker at 225 rpm. Duplicate 3 ml samples were pelleted by centrifugation for 10 minutes at 2500 rpm in a Varifuge™ (Heraeus Instruments). Supernatant was aspirated and discarded, and the pellets frozen (–80° C. for 10 minutes). Tubes containing the frozen pellets were then placed in a Labconco™ lyophilizer for 20 minutes, or until samples were freeze-dried.

One point seven milliliters of ACS grade methanol (Mallinckrodt), 2 ml ACS grade chloroform (Mallinckrodt), 0.3 ml concentrated sulfuric acid (added while vortexing tube), and 0.1 ml benzoic acid solution (2 mg/ml) was added to each of the tubes. Samples were capped tightly, placed in a heat-block adjusted to 100° C., and incubated for 140 minutes. Samples were then removed from the heat-block and allowed to cool to room temperature. One milliliter of deionized water was then added to each tube, and the tubes were vortexed for 30 seconds, followed by centrifugation for 10 minutes at 2500 rpm. The upper aqueous phase and protein interface of each sample was aspirated off, and the remaining organic phase was pipetted into vials and assayed for PHB production by gas chromatography.

C. Gas Chromatography

A Shimadzu GC-14A connected to a CR-4A data processing unit, an AOC-14 autoinjector and an AOC-1400 autosampler were utilized for gas chromatography. The carrier gas was helium and detection was through a flame ionization detector. Flow rate of the carrier was approximately 5 ml/min. The column used for detection was a Supelcowax 10 column from Supelco Separation Technologies. The column was a 15 meter column, 0.53 mm inner diameter, with a 1 µm thick coating.

Samples (1 to 3 µl) were injected into the injection port (temperature 200° C.) and carried into the column. The samples were run under a temperature profile of 55° C. for 5 minutes, followed by a temperature ramp of 5° C. per minute until the column temperature reached 220° C. The temperature was held at 220° C. for 5 minutes, followed by termination of the run and cool-down for the next run. Typically, the solvent peak eluted through the detector (240° C.) between 1 and 2 minutes, and the PHB peak eluted between 3 and 4 minutes. Analyses were performed utilizing benzoic acid (100 µl of 2 mg/ml solution in methanolysis tubes) as an internal standard. Typically, benzoic acid eluted from the GC column approximately 5 minutes into the run.

D. Calculation of PHB Concentration

As a control, PHB samples of various weights were subjected to methanolysis, and the area under each curve (integration by Shimadzu data processor) was graphed versus the known weight. The resulting line was utilized to generate an equation that could be used in calculating the PHB content of unknowns, using the integration area under the PHB peak.

Figure 4:
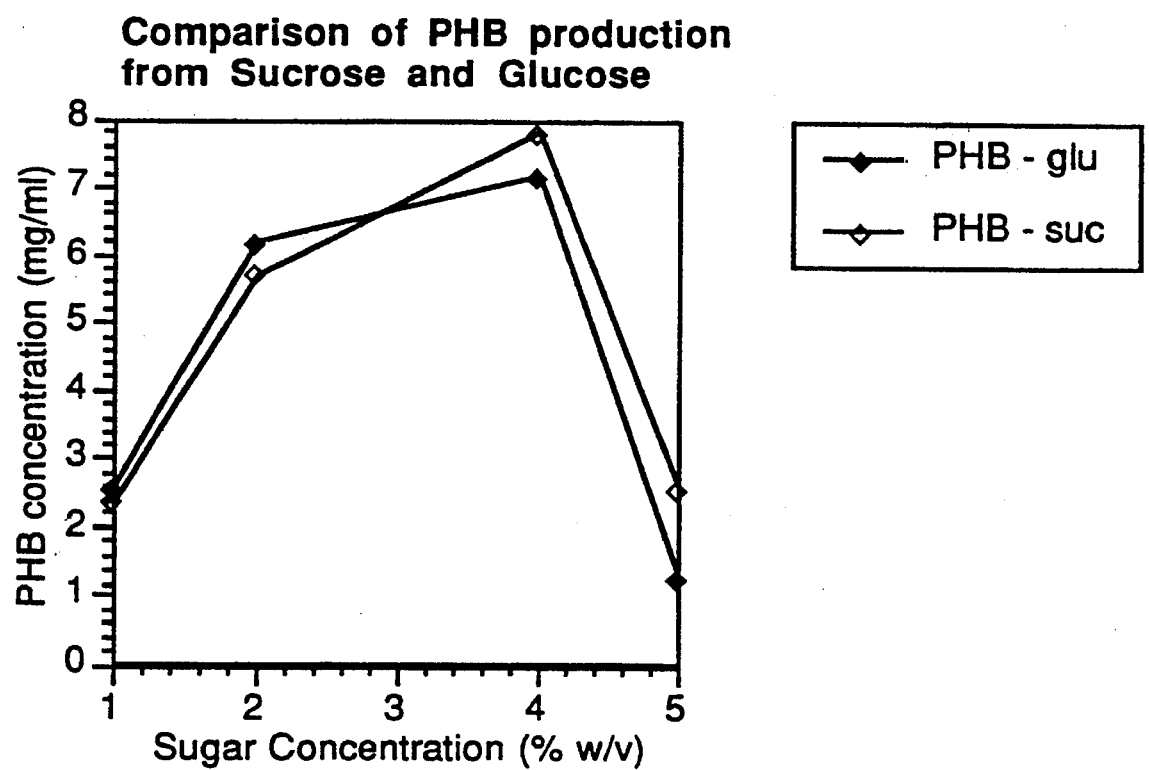
FIG. 4 is a graph which depicts PHB production in JMU 213 (pJM9131) at different concentrations of glucose or sucrose.

The PHB production from different concentrations of glucose and sucrose in JMU 213 (pJM9131) is shown in FIG. 4. Briefly, PHB production was highest at 4% sugar for both glucose and sucrose. Sucrose utilization yielded approximately the same amount of polymer as glucose utilization. At higher sugar concentrations, sucrose utilization outperforms glucose utilization.

EXAMPLE 5

Comparison of Sucrose and Glucose Utilization For JMU 213 (pJM9131) and *E. coli* K12 (pJM9131)

Plasmid pJM9131 was electroporated into *E. coli* JMU 213 and *E. coli* K12 (ATCC No. 53704) (which does not contain a sucrose utilization plasmid) essentially as described in Example 2. JMU 213 (pJM9131) and *E. coli* K12 (pJM9131) were then inoculated into separate 250 ml shake-flask cultures containing 50 ml of LB and 50 µg/ml kanamycin, and grown overnight in an orbital shaker (225 rpm) at 37° C. One milliliter of culture was inoculated into each of two sterilized, baffled 250 ml Erlenmeyer culture flask containing 50 ml of M9 minimal medium and kanamycin (50 µg/ml), and either 2% glucose or 2% sucrose. Three milliliter samples of the cultures were taken at 1, 2, 6.5, 8.5, and 24 hours. Samples were prepared for methanolysis and analyzed by gas chromatography as described above in Example 4.

Figure 5:
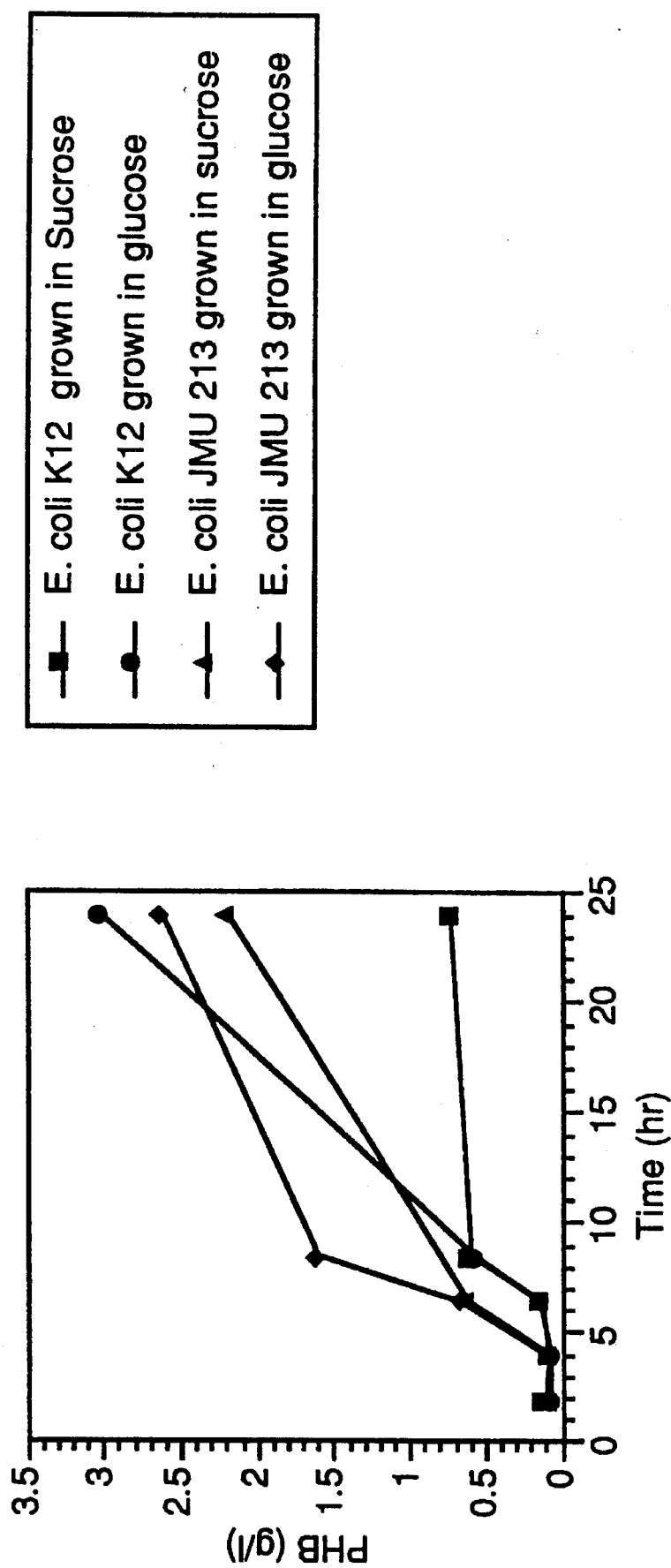
FIG. 5 is a graph which depicts PHB production in *E. coli* JMU 213 and *E. coli* K12 over time, in cultures grown in and glucose or sucrose.

PHB production from sucrose and glucose in *E. coli* JMU 213 and *E. coli* K12 is shown in FIG. 5. Briefly, the final PHB yield (mg/ml) was highest for both JMU 213 and K12 on glucose. On sucrose, however, JMU 213 yielded nearly as much PHB as on glucose, and more than twice as much as K12 on sucrose.

EXAMPLE 6

Comparison of PHB Production in JMU 212 and JMU 213

JMU 212 is a wild type strain of *Klebsiella aerogenes*, and was obtained from Dr. Robert Bender at University of Michigan. This strain is a derivative of KC1043 hutC515 (see O'Neill et al., *J. Bact.* 159:388–389, 1984) due to a deletion in the chromosomal ampicillin gene. pJM9131 (described above) was introduced by electroporation (as described in Example 2) into JMU 212.

JMU 212 (pJM9131) and JMU 213 (pJM9131) (from plate cultures) were inoculated into a sterile 250 ml baffled Erlenmeyer culture flask containing 50 ml of LB, 50 µg/ml kanamycin, and either 2% glucose or 2% sucrose. All four flasks were incubated 24 hr at 37° C. in an orbital shaker at 225 rpm. Three milliliter samples were taken from each flask and analyzed by methanolysis and gas chromatography as described in Example 4.

Figure 6:
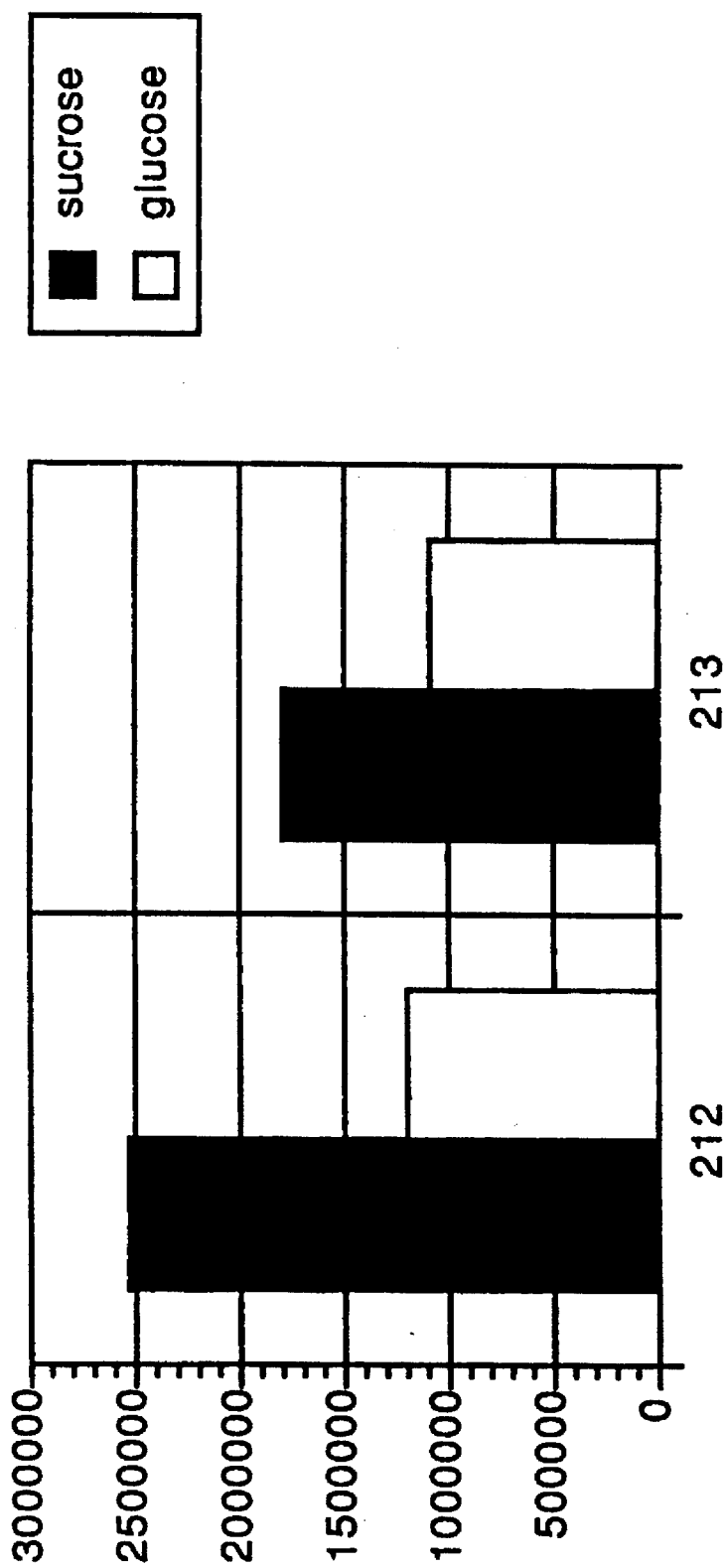
FIG. 6 is a bar graph which depicts PHB production in JMU 212 and JMU 2 13, grown in glucose or sucrose.

PHB production in JMU 212 (p9131) and JMU 213 (9131) is shown in FIG. 6. Briefly, JMU 212 makes more PHB from sucrose than from glucose. In addition, JMU 212 makes more PHB than JMU 213 on either substrate.

EXAMPLE 7

*Klebsiella aerogenes* (pJM9131) Produce PHB at Various Sucrose Concentrations

*Klebsiella aerogenes* JMU 212 (pJM 9131) was grown at different concentrations of sucrose in order to determine PHB production at various concentrations. The production of PHB was monitored and compared to that of JMU 213 (pJM 9131).

Briefly, cells were inoculated in 3 ml of LB containing kanamycin (50 µg/ml), and incubated overnight at 250 rpm and 30° C. (for Klebsiella), or 37° C. (for *E. coli*). One milliliter of the overnight culture was transferred into 50 ml of M9 medium supplemented with thiamine (0.5 mg/L), casamino acids (1 g/l), kanamycin (50 μg/ml), and different concentrations of sucrose, and then incubated in 250 ml baffled shake flasks at 30° C. (for Klebsiella) or 37° C. (for *E. coli*). After 24 hours, 2 ml cultures were withdrawn, the medium removed by centrifugation, the cell pellet dried in a lyophilizer, methanolized, and subjected to GC analysis as described in Example 4.

Figure 7:
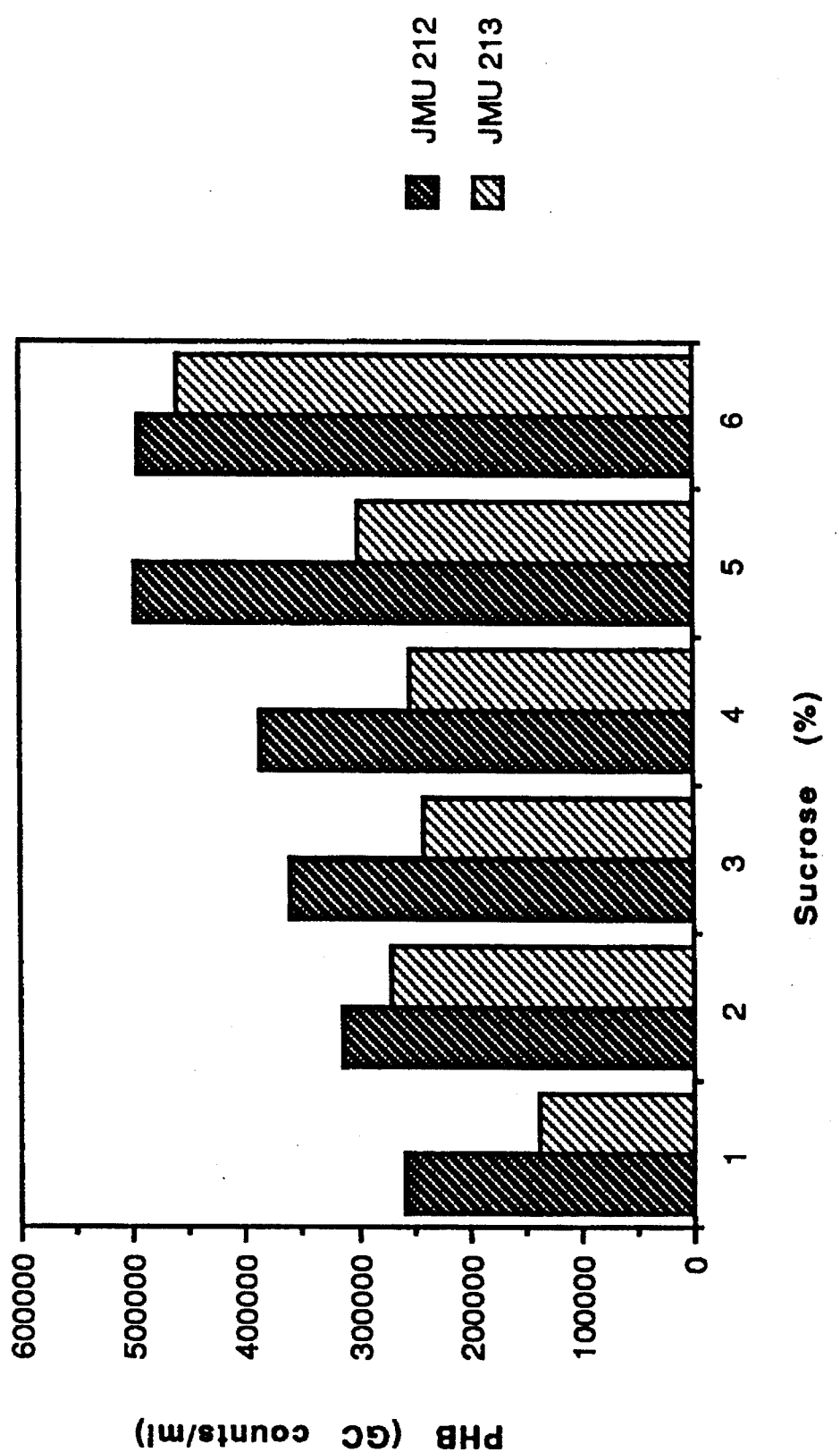
FIG. 7 is a bar graph which depicts PHB production at various sucrose concentrations by JMU 212 (pJM9131) and JMU 213 (pJM9131).

As shown in FIG. 7, for all concentrations of sucrose tested (1%–6%), *Klebsiella aerogenes* JMU212 (pJM9131) produced more PHB than JMU 213 (pJM 9131).

EXAMPLE 8

Glucose and Sucrose Uptake by *Klebsiella aerogenes* (pJM 9131)

The uptake of 14C-sucrose and 14C-glucose by *Klebsiella aerogenes* (pJM 9131) were measured and compared to that of JMU 213 (pJM 9131) in the following experiment. Briefly, cells were inoculated in 3 ml of LB containing kanamycin (50 μg/ml) and 0.5% sucrose (for the sucrose uptake assay) or 0.5% glucose (for glucose uptake), incubated overnight at 250 rpm and 30° C. (for Klebsiella) or 37° C. (for *E. coli*). One milliliter of the overnight culture was transferred into 50 ml of M9 medium supplemented with thiamine (0.5 mg/l), casamino acids (1 g/l), kanamycin (50 μg/ml), and 0.5% sucrose or 0.5% glucose, and then incubated at 250 rpm and 30° C. for (Klebsiella) or 37° C. (for *E. coli*) in 250 ml baffled shake flasks for about 4 hours. One milliliter of the culture was removed and centrifuged, the supernatant aspirated, washed again with 1 ml of M9 medium, and resuspended in M9 medium to a final optical density of 1 at 600 nm. One-half of a milliliter containing the cell suspension was then incubated in M9 medium at 30° C. Two micro-Curies of $^{14}C$-sucrose (632 mCi/mmol, 0.5 μCi/μl) or 1 μCi $^{14}C$-glucose (320 mCi/mmol, 0.5 μCi/μl)) was then added to the culture. At indicated time intervals, 80 ml samples were withdrawn and immediately applied to membrane filters (0.2 μm) in order to remove medium containing the radioactive material. The membranes were then washed twice with 1 ml of M9 medium and air dried. The radioactive material attached to the membrane was then measured in 5 ml of Scintiverse by a Beckman LS 5000TA scintillation counter.

Figure 8B:
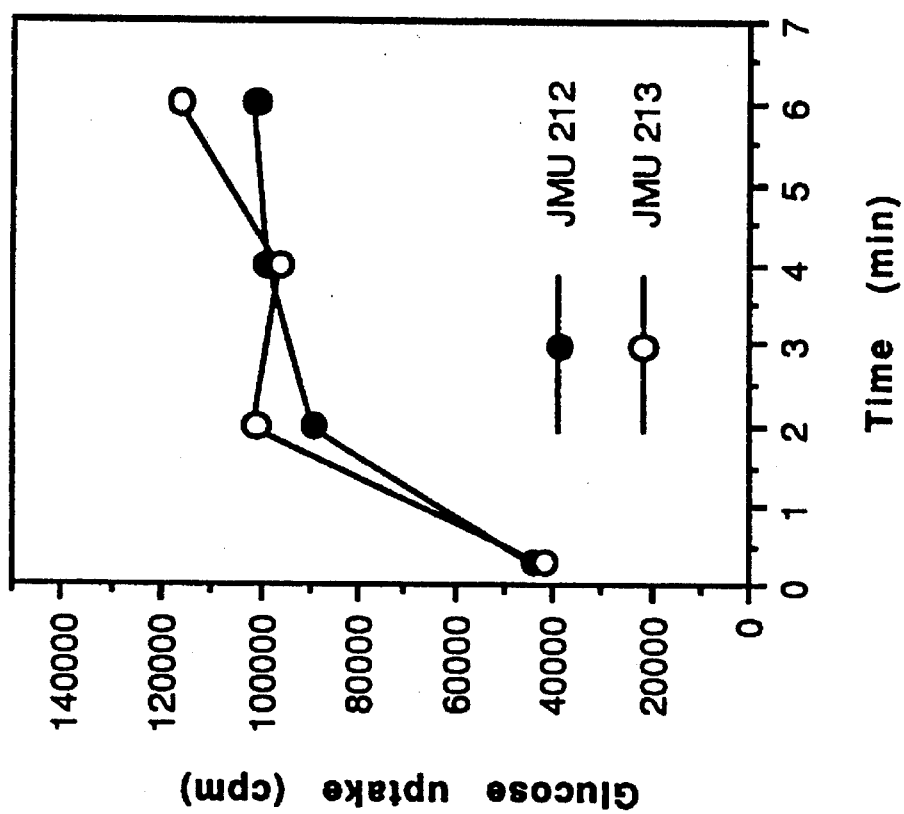
FIGS. 8A and 8B are two graphs which depict sucrose and glucose uptake by JMU 212 (pJM9131) and JMU 213 (pJM9131).
Figure 8A:
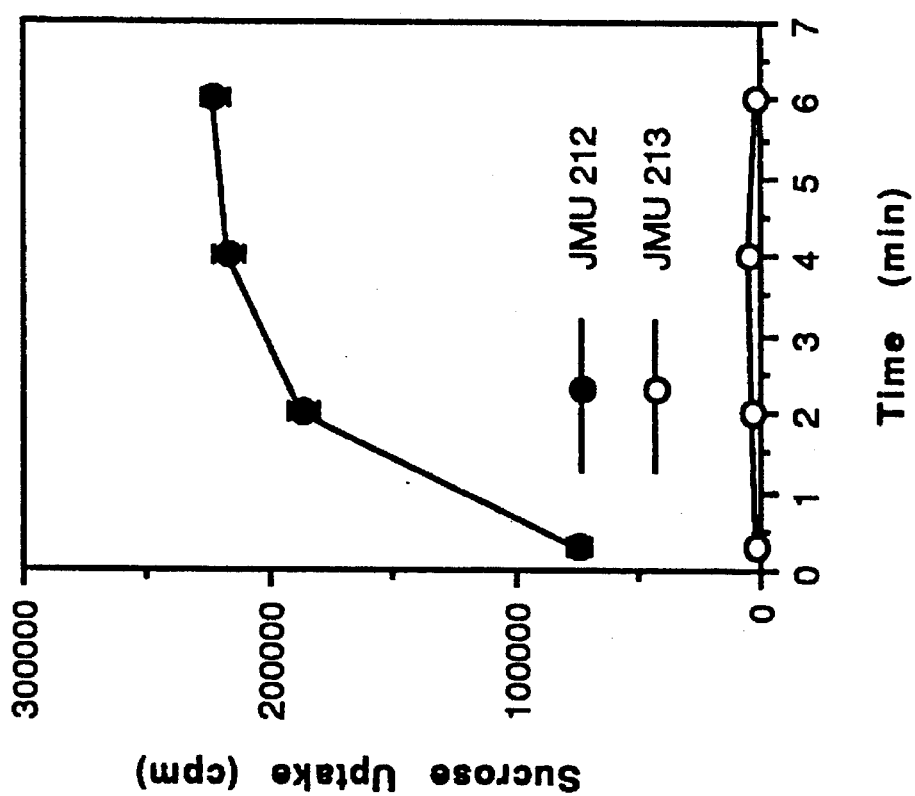

As shown in FIGS. 8A and 8B, glucose uptake rates for both JMU 212 and JMU 213 are comparable. However, sucrose uptake is much better in JMU 212 than in JMU 213.

EXAMPLE 9

Sucrose Uptake of JMU 212 (pJM9131) at Different Sucrose Concentrations

Since the uptake rate varies at different concentrations of the substrate, the sucrose uptake at various concentrations of sucrose was measured in order to ensure a more thorough comparison.

Briefly, cells were inoculated in 3 ml of LB containing kanamycin (50 μg/ml), and incubated overnight in an orbital shaker (250 rpm) at 30° C. One milliliter of the overnight culture was transferred into 50 ml of M9 medium supplemented with thiamine (0.5 mg/l), casamino acids (1 g/l), kanamycin (50 μg/ml), and 0.5% sucrose; and incubated in shaking flasks for about 4 hours. Five milliliters of the cell culture was then dried and weighed. One milliliter of the culture was centrifuged at 3000 rpm for 10 minutes (Heraeus Varifuge), the supernatant aspirated, and the pellet washed again with 1 ml of M9 medium, followed by resuspension in M9 medium to a final optical density (600 nm) of 1. One-half of a milliliter of the cell suspension was then incubated at 30° C., and $^{14}C$-sucrose was added to the cells the indicated concentrations. At indicated time intervals, 80 μl samples were withdrawn and processed as above.

Figure 9:
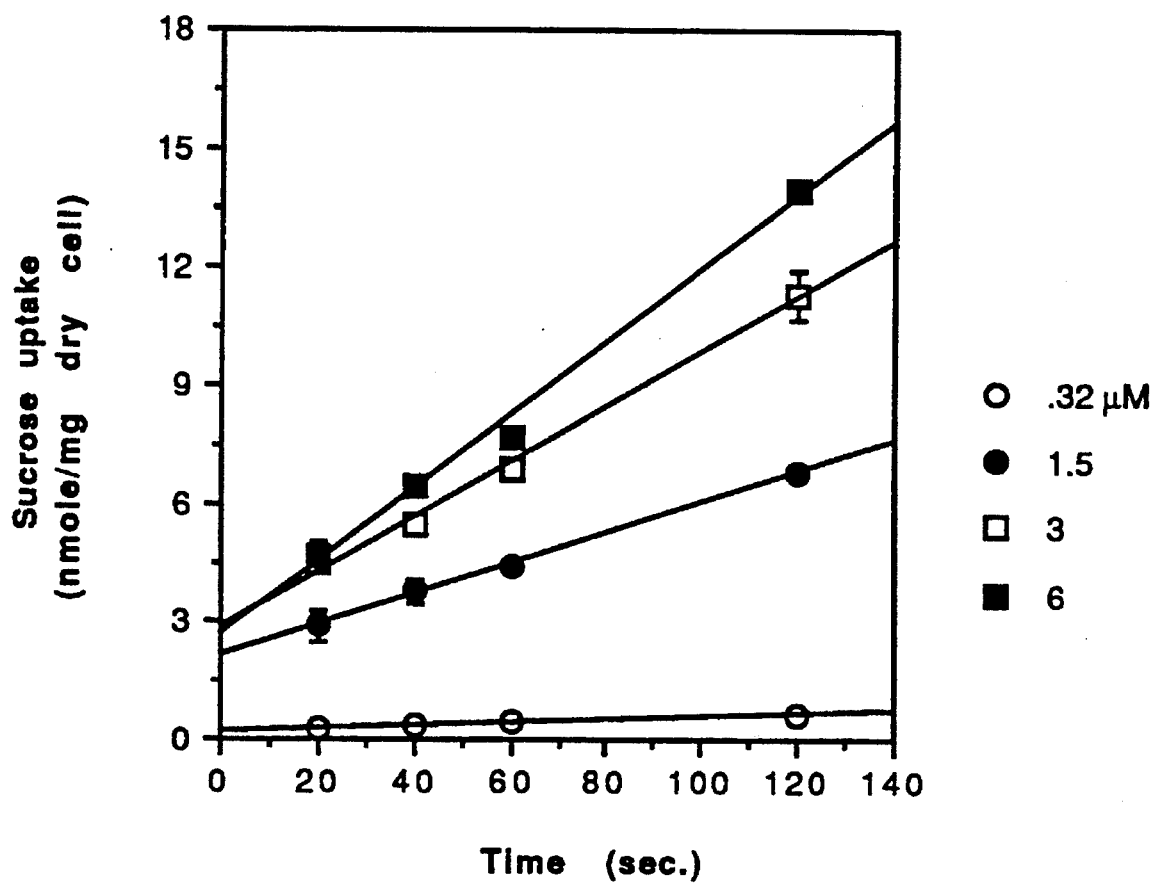
FIG. 9 is a graph which depicts sucrose uptake by JMU 212 (pJM9131) at different sucrose concentrations.

As shown in FIG. 9, the rate of sucrose uptake by *Klebsiella aerogenes* (pJM9131) increased as the sucrose concentration increased in the concentration range tested (0.32 μM to 6 μM).

EXAMPLE 10

Medium Optimization

The results described above suggested that *Klebsiella aerogenes* (pJM9131) may be useful for the production of PHB utilizing sucrose as carbon source.

A series of different minimal media was also screened in order to optimize the conditions for PHB production using sucrose as major carbon source. Briefly, *Klebsiella aerogenes* (pJM9131) from plate culture was inoculated into 3 ml of LB containing kanamycin (50 μg/ml), incubated overnight at 250 rpm and 30° C. Two milliliters of the overnight culture was transferred into 50 ml of each medium described below and incubated at 250 rpm and 30° C. in 250 ml baffled shake flasks.

Medium 1: 10.5 g $K_2HPO_4$, 4.5 g $KH_2PO_4$, 3 g $(NH_4)_2SO_4$, 20 g sucrose, 50 mg kanamycin in one liter solution.

Medium 2: 10.5 g $K_2HPO_4$, 4.5 g $KH_2PO_4$, 3 g $(NH_4)_2SO_4$, 0.1 g $MgSO_4$, 20 g sucrose, 50 mg kanamycin in one liter solution.

Medium 3 10.5 g $K_2HPO_4$, 4.5 g $KH_2PO_4$, 3 g $(NH_4)_2SO_4$, 0.1 g $MgSO_4$, 0.5 g casamino acids, 20 g sucrose, 50 mg kanamycin in one liter solution.

Medium 4 10.5 g $K_2HPO_4$, 4.5 g $KH_2PO_4$, 3 g $(NH_4)_2SO_4$, 0.1 g $MgSO_4$, 0.5 g casamino acids, 2 ml trace element solution, 20 g sucrose, 50 mg kanamycin in one liter solution.

Medium 5 10.5 g $K_2HPO_4$, 4.5 g $KH_2PO_4$, 3 g $(NH_4)_2SO_4$, 0.1 g $MgSO_4$, 0.5 g casamino acids, 2 ml trace element solution, 20 mg $CaCl_2$, 20 g sucrose, 50 mg kanamycin in one liter solution.

Medium 6 10.5 g $K_2HPO_4$, 4.5 g $KH_2PO_4$, 3 g $(NH_4)_2SO_4$, 0.1 g $MgSO_4$, 0.5 g casamino acids, 2 ml trace element solution, 20 mg $CaCl_2$, 5 mg $FeSO_4$, 20 g sucrose, 50 mg kanamycin in one liter solution.

Two milliliters of culture was withdrawn from each of the flasks after incubation for 24 and 48 hours, the medium removed by centrifugation (3,000 rpm×10 min), the cell pellet dried in a lyophilizer, methanolized, and subjected to GC analysis as described above. As shown in Table 1, medium 4 appeared to give the best results.

TABLE 1

| | (GC counts/ml culture) | |
|---|---|---|
| Medium | 24 hours | 48 hours |
| 1 | 73391 | 98794 |
| 2 | 328528 | 686072 |
| 3 | 662112 | 1114109 |
| 4 | 842447 | 1149900 |
| 5 | 731235 | 1121614 |
| 6 | 671618 | 733210 |

EXAMPLE 11

PHB Production of *Klebsiella aerogenes* (pJM9131) Using Molasses as Carbon Source Using Medium 4, high-test molasses was tested as carbon source instead of pure sucrose. (See FIGS. 10A and 10B, 11, and 12). Briefly, *Klebsiella aerogenes* (pJM9131) from plate culture was inoculated in 3 ml of LB containing kanamycin (50 µg/ml) and incubated overnight at 250 rpm and 30° C. Two milliliters of the overnight culture ($OD_{600}$= 3.74) was transferred into 50 ml of Medium 4 described above with or without casamino acids. High-test molasses was used as carbon source at a final concentration of 5%. The cultures were then incubated in 250 ml baffled shake flasks at 250 rpm, 30° C. At different time points, optical density at 600 nm was determined, and 2 ml cultures were withdrawn, the medium removed by centrifugation, the cell pellet dried in lyophilizer, methanolized, and subject to GC analysis as above.

Figure 10A:
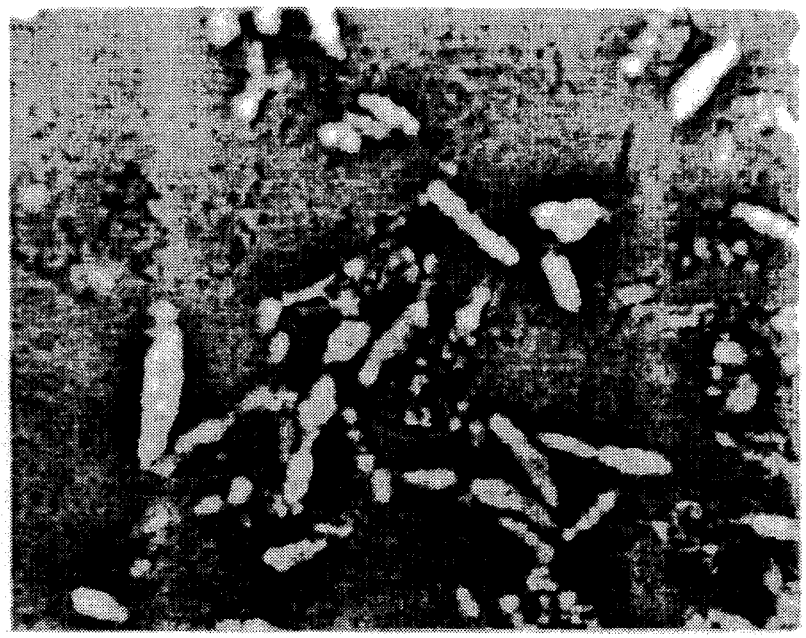
FIGS. 10A and 10B are micrographs of *Klebsiella aerogenes* (pJM9131) showing high levels of intracellular PHB.
Figure 10B:
Figure 11:
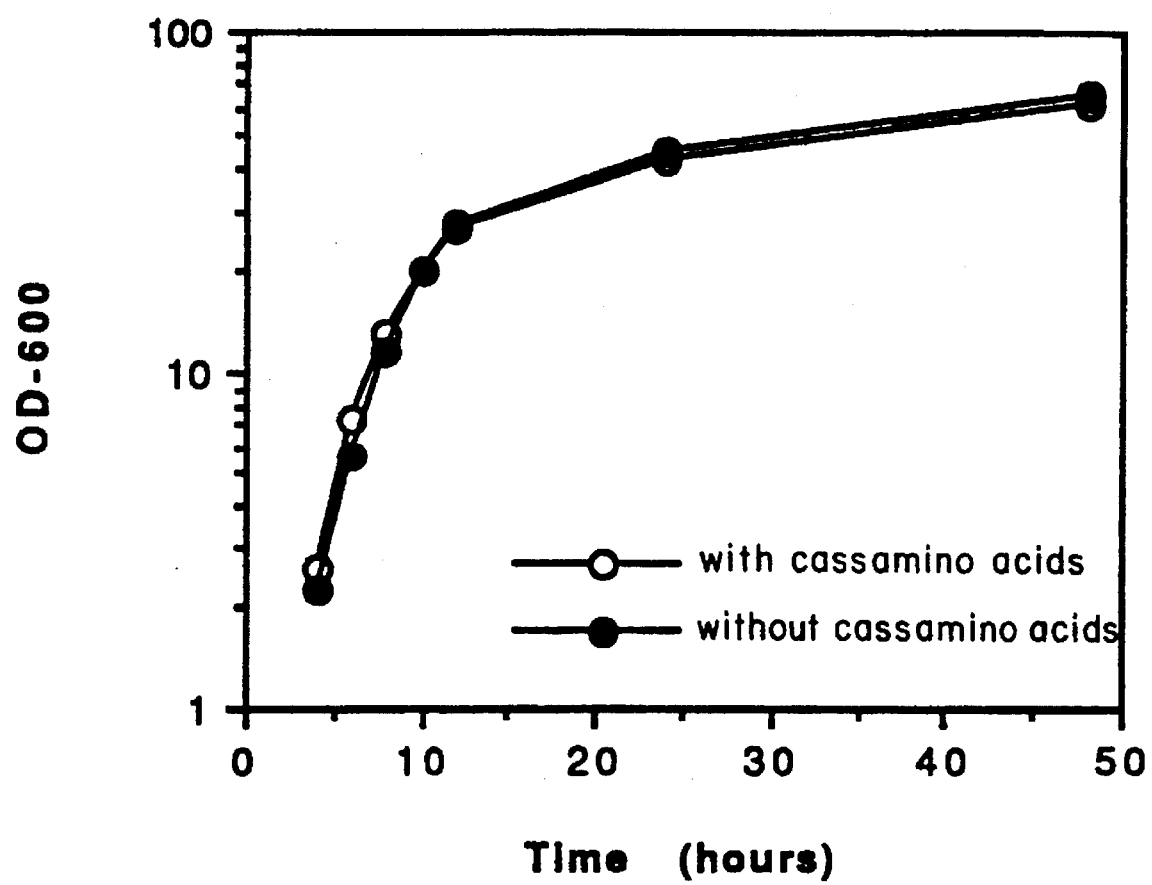
FIG. 11 is a graph which depicts the optical density (600 nm) of two cultures, one with casamino acids, the other without.
Figure 12:
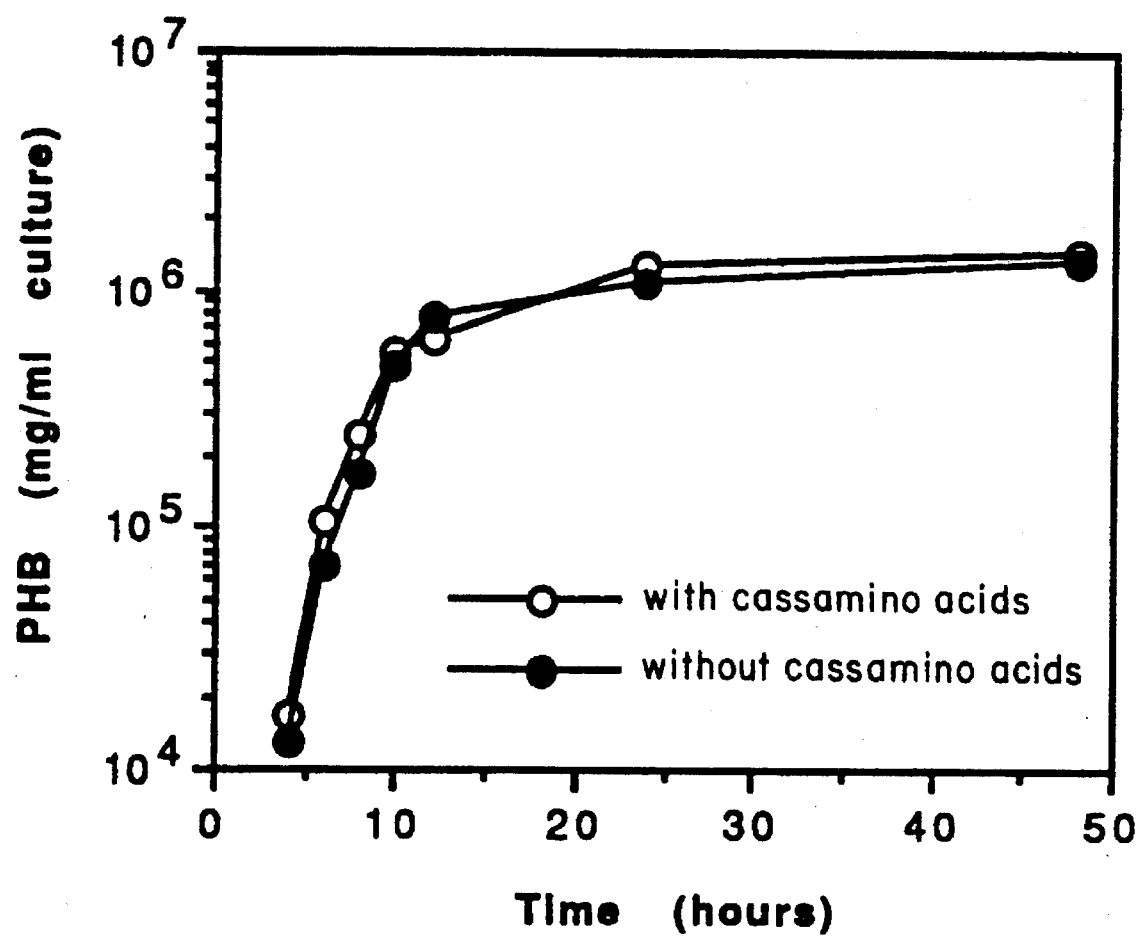
FIG. 12 is a graph which depicts PHB production in two cultures, one with casamino acids, the other without.

The results are shown in FIGS. 10–12. Briefly, FIGS. 10A and 10B are micrographs of *Klebsiella aerogenes* (pJM9131) showing high levels of intracellular PHB. PHB levels are estimated to be greater than 90%. PHB granules are seen as light areas in the cell because they do not take up the dye. FIG. 11 is a graph which depicts the optical density (600 nm) of two cultures, one with casamino acids, the other without. FIG. 12 is a graph which depicts PHB production in two cultures, one with casamino acids, the other without.

When high-test molasses was used as carbon source, high level of cell growth and PHB production was achieved with or without supplementing the medium with casamino acids.

EXAMPLE 12

Fermentation of *Klebsiella aerogenes* (pJM9131) Using Molasses as Carbon Source Fermentation of *Klebsiella aerogenes* (pJM9131) was performed in order to determine the potential of PHB production at larger scale. Briefly, *Klebsiella aerogenes* (pJM9131) from a plate culture was inoculated into 3 ml of LB containing kanamycin (50 µg/ml), and incubated overnight at 250 rpm and 30° C. Two milliliters of the overnight culture was transferred into 250 ml of LB containing kanamycin (50 µg/ml), and incubated overnight at 250 rpm and 30° C. This 250 ml culture then was inoculated into a Braun Biostate E fermenter containing 4 liters of Medium 4 without casamino acids, and with high-test molasses at a concentration of 5% (sterilized in the fermenter for 30 minutes prior to inoculation). Fermenter parameters were set up as follows: pH=7, temperature=30° C., maximum stirring speed=800 rpm, dissolved oxygen level = 80% of the saturation. After the sterilized medium cooled down to 30° C., kanamycin was added to a final concentration of 50 mg/l, and the 250 ml culture was inoculated aseptically. 6M NaOH was used to neutralize the acid produced during the fermentation. Substrate feeding was turned on after 10 hours fermentation, and the feed rate was adjusted according to the alkali consumption. Feeding substrate had following composition: 50 g $(NH_4)_2SO_4$, 2.5 g $MgSO_4$, 0.5 ml trace element solution, and 500 ml of molasses in 1000 ml solution. About 30 ml of sample was withdrawn at indicated time intervals, and used to measure the biomass and PHB production level as described above.

Figure 13:
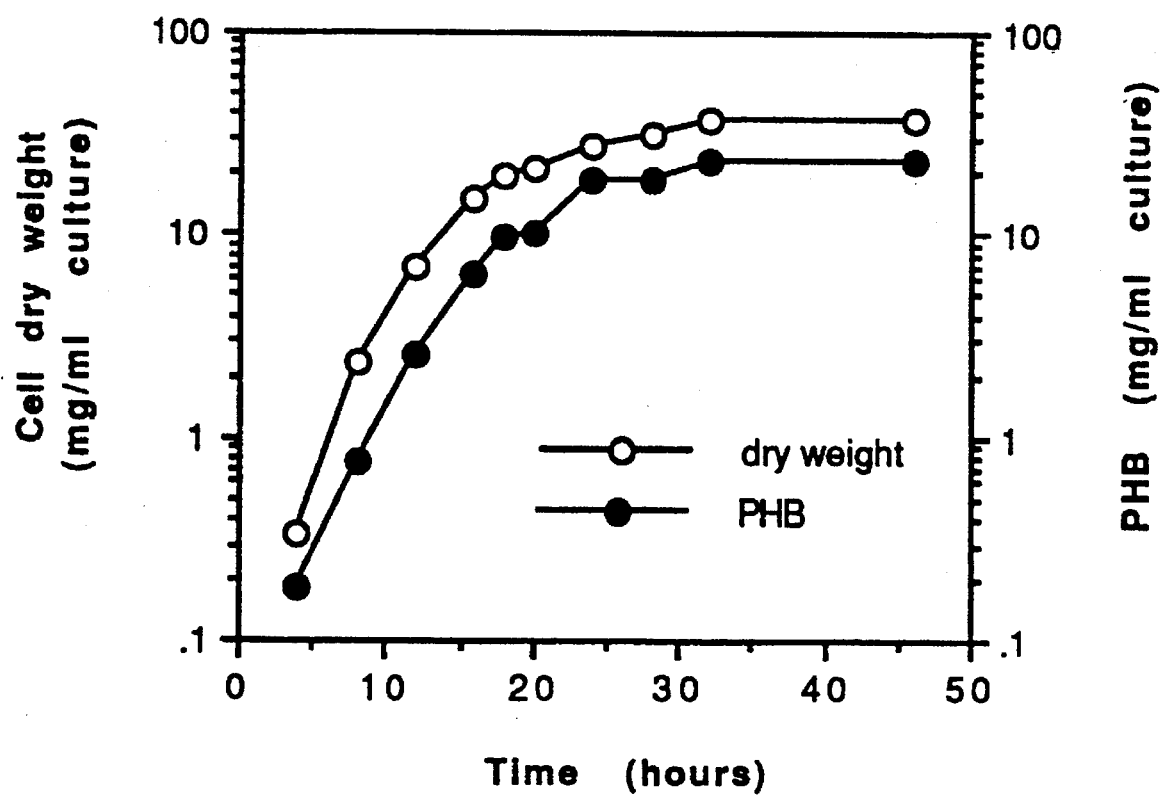
FIG. 13 is a graph which depicts cell dry weight and PHB content vs. fermentation time.

As shown in FIG. 13, (a graph which shows cell dry weight and PHB vs. fermentation time), *Klebsiella aerogenes* is capable of producing commercially important amounts of PHB in a fermenter.

EXAMPLE 13

Construction of a *Klebsiella oxytoca* M5a1 fadR::kan Strain by Transduction A plasmid containing the fadR gene and a kanamycin resistance gene was transduced into Klebsiella, and then tested for its ability to produce the PHB-co-V copolymer essentially as described below. The experimental protocol utilized is essentially described in "A Short Course in Bacterial Genetics," by Jeffrey H. Miller, Cold Spring Harbor Laboratory Press, Experiment 19, pages 271–274, 1992.

Briefly, a standard P1vir phage stock was used to prepare a transducing lysate of *E. coli* CAG18544 fadR::Tn10kan (obtained from Carol Gross at the University of Wisconsin; see Singer et al., *Microbiological Reviews* 53(1):1–24, 1989). In particular, an overnight culture (inoculated from an isolated colony on plate into 3 ml of LB in tube, and grown at 37° C., 225 rpm) was made, and in the morning 30 µl of the overnight culture was transferred to a 3 ml tube of LB containing 0.005M calcium chloride and 0.2% glucose. After 1 hour in a water bath without aeration, 100 µl of P1vir was added. The cells were incubated 2–3 hours at 37° C. until they appeared to be lysed (clearing of the culture). At this time several drops of chloroform were added, the tube was vortexed, and then centrifuged for 10 minutes at 2,000 rpm in a Heraeus Varifuge centrifuge. The supernatant was removed to a new tube, and several drops of chloroform were added. The lysate was stored at 4° C.

To transduce the fadR mutation into *K. oxytoca* M5a1 (obtained from Gary Roberts, Univ. of Wisconsin), an overnight culture of *K. oxytoca* (isolated colony from plate into 3 ml tube culture of LB) was centrifuged in the Heraeus Varifuge centrifuge (2,500 rpm for 10 minutes). The pellet was resuspended in 3 ml of MC buffer (0.1M magnesium sulfate, 0.005M calcium chloride). One hundred microliters of cells were added to a sterile microcentrifuge tube, and 100 µl of P1vir transducing lysate (as described above) was mixed with the cells, and incubated at 37° C. for 20 minutes. After 20 minutes, 200 µl of 100 mM sodium citrate was added. The cells were then pelleted in a microcentrifuge (20 seconds×14,000 g), the supernatant aspirated, and the pellet resuspended in 500 µl of LB containing 50 mM sodium citrate. The cells were then pelleted and resuspended as above, and incubated for 45 minutes at 37° C. After this, 200 µl of cells were spread onto Luria agar plates containing 10 µl/ml kanamycin, and the plates were incubated at 34° C. for 2 days. Several large colonies that grew on the plates were selected. One of these, designated *K. oxytoca* fadR::Tn10kan, was utilized in further studies described below.

EXAMPLE 14

PHB-co-V Production in *Klebsiella oxytoca* M5a1 fadR:Tn10kan (pJM9131)

In order to determine the effect of increasing propionate concentrations on PHB-co-V production in the above-identified *Klebsiella oxytoca*, the following experiment was conducted. Briefly, 50 ml LB (100 µg/ml kanamycin) cultures in 250 ml baffled flasks were inoculated from an isolated colony on a Luria agar plate (containing kanamycin as above). The culture was grown overnight at 30° C., 225 rpm on a Labconco orbital shaker incubator. The next day, 1 ml of this culture was inoculated into each of 4 flasks containing M9 minimal medium, kanamycin (100 μg/ml), and 1% glucose (Sigma chemicals). In addition, each flask contained either 0, 1, 5 or 10 mM propionate. The flasks were grown for 24 hr, and 3 ml was harvested from each and tested for polymer production by gas chromatography as described above in Example 4.

Figure 14:
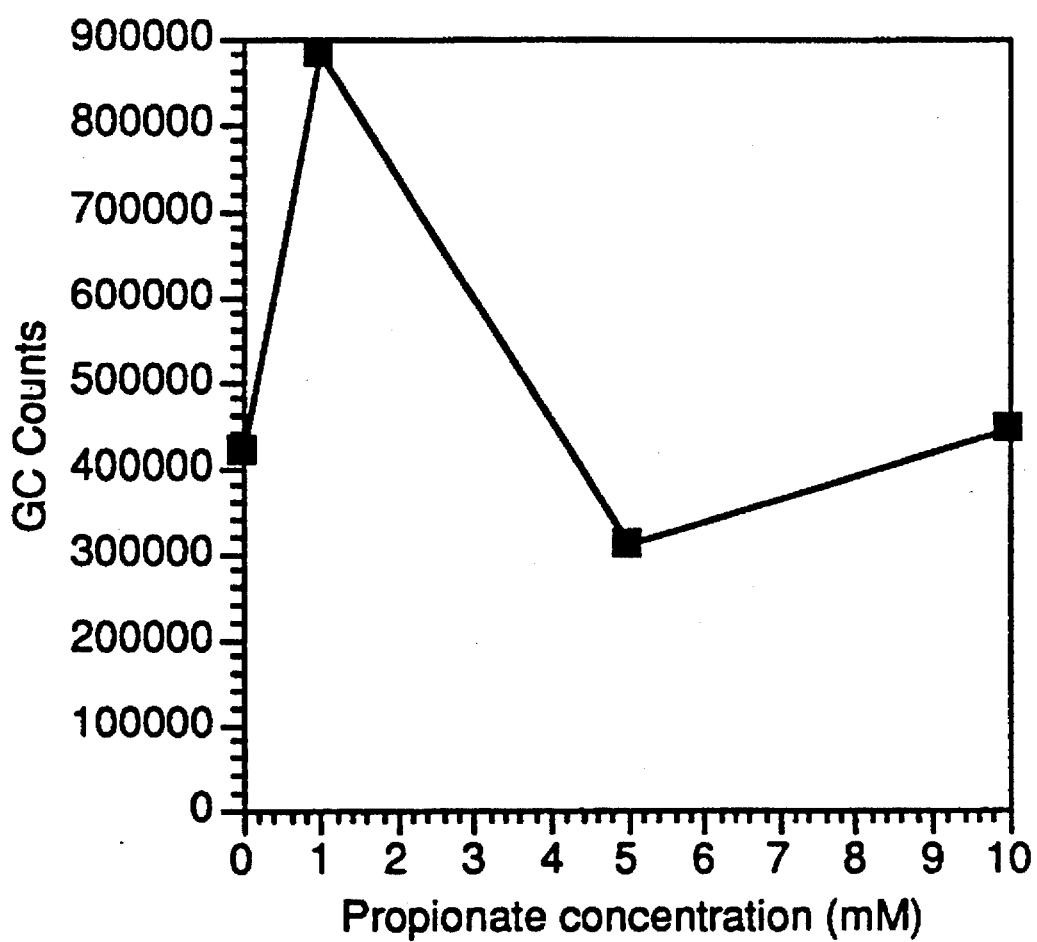
FIG. 14 is a graph which depicts total polymer produced as a function of propionate concentration in medium.
Figure 15:
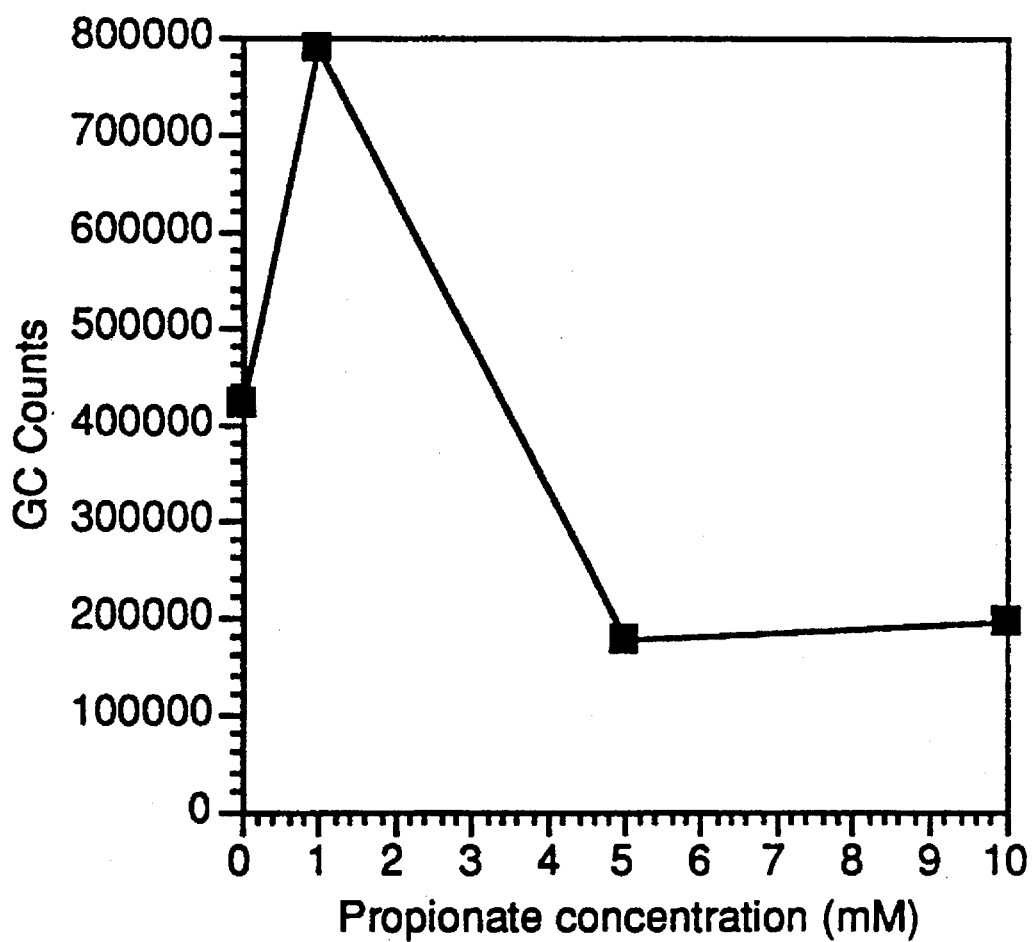
FIG. 15 is a graph which depicts 3-hydroxybutyrate produced as a function of propionate concentration in medium.
Figure 16:
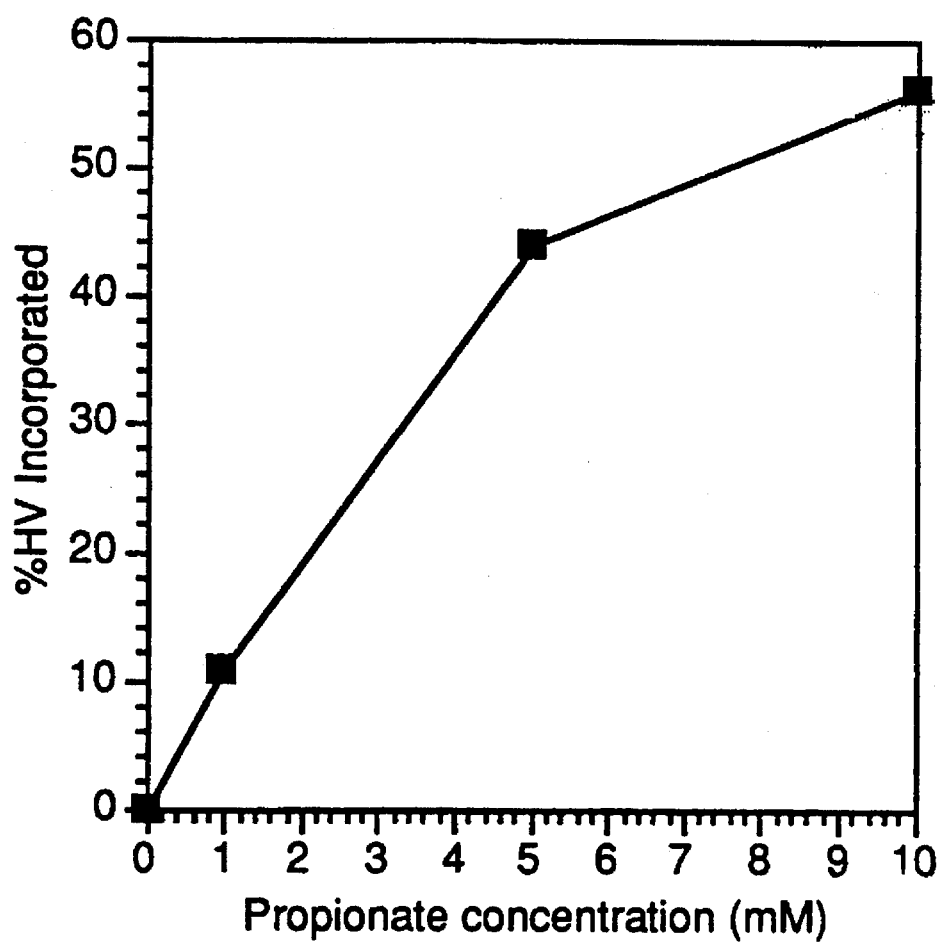
FIG. 16 is a graph which depicts the percentage of 3-hydroxyvalerate in the PHB-co-V copolymer as a function of propionate concentration in medium.

Results are shown in FIGS. 14, 15, and 16, and are given in GC integration units. In particular, FIG. 14 is a graph which depicts the total polymer production as a function of propionate concentration in medium. FIG. 15 is a graph which depicts 3-hydroxybutyrate produced as a function of propionate concentration in medium. FIG. 16 is a graph which shows the percentage of 3-hydroxyvalerate in PHB-co-V copolymer, as a function of propionate concentration in medium. From these figures, it is evident that as the propionate concentration rises, the PHB amount decreases, as does the total polymer. The hydroxyvalerate fraction of the polymer, however, rises with increasing propionate concentration in the medium. For example, at 5 mM propionate PHV it was 43% of total polymer, and at 10 mM propionate it was 56% of total polymer.

EXAMPLE 15

Effect of Propionate Feeding Strategy on Polymer Synthesis in *Klebsiella oxytoca* M5al (pJM9116)

Since propionate is toxic to cells (see the above experiment), and therefore detrimental to total polymer production, the following experiment was performed in which propionate was added to the medium at different times.

Plasmid pJM9116 was electroporated into *K. oxytoca* M5al essentially as described in Example 2A. A clone was isolated from the electroporated cells by growing them on LB plates containing 1% sucrose at 34° C. Under these conditions, clones producing PHB are easily discerned because they are considerably whiter than PHB nonproducers. An isolated colony of *Klebsiella oxytoca* M5al (pJM9116) was selected from the plate, inoculated into 3 ml tube cultures of LB (25 μg/ml chloramphenicol ["CAM"]), and grown overnight in an orbital shaker (225 rpm) at 32° C. The next day, the overnight culture was pelleted and resuspended in 1 ml of M9 minimal media. Two hundred and fifty microliters of the resuspended pellet was added to each of 4 flasks:

A. M9 minimal+ 1% glucose+ 25 μg/ml CAM

B. As in flask "A"+ 5 mM propionate

C. As in flask "A"

D. As in flask "A"

The four flasks were grown at 34° C., 225 rpm on an orbital incubator. Propionate concentration in flask "C" was increased in 1 mM amounts at time 0 (time of inoculation), 0.5, 1, 1.5, and 2 hours (for a final total concentration of 5 mM). Propionate was added to flask "D" (final concentration= 5 mM), when it reached an optical density of 2. The cultures were allowed to grow for 48 hours, and then 3 ml samples were taken from each culture, lyophilized, and the polymer content determined by gas chromatography as described in Example 4.

Figure 17:
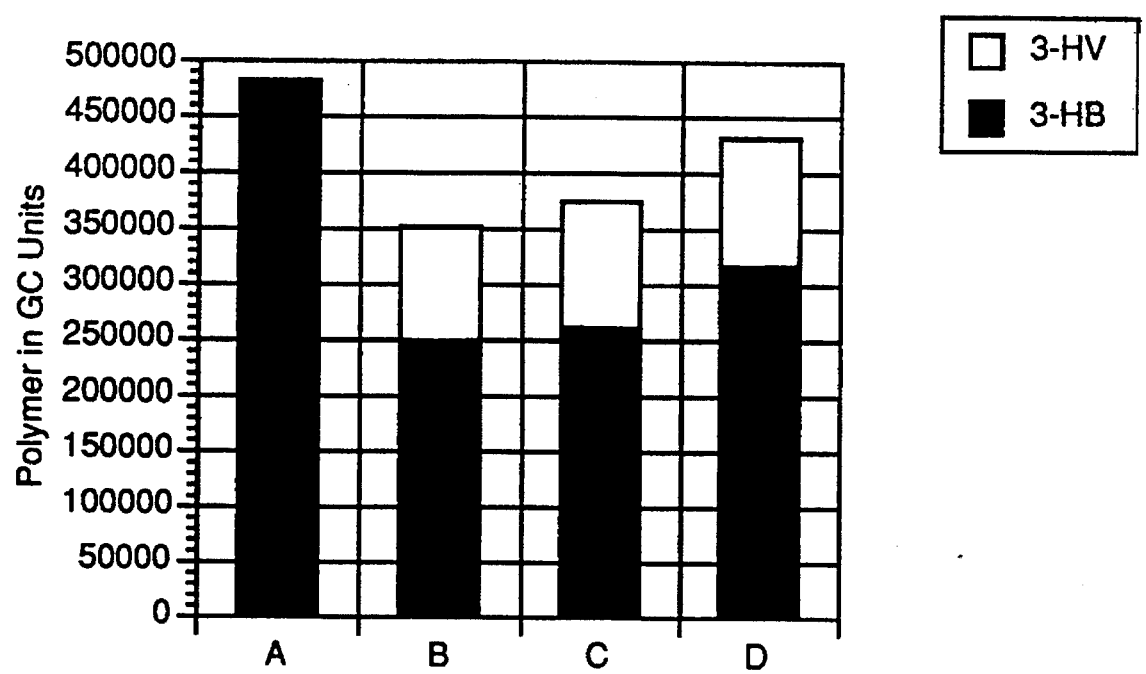
FIG. 17 is a bar graph which shows total polymer and 3-hydroxyvalerate content accumulated under different feeding strategies.

As shown in FIG. 17 (results are given in GC integration units), without propionate addition, no PHB-co-V was made. If propionate addition is delayed until the culture reaches late log phase ($OD_{600}$= 2), total polymer and hydroxyvalerate incorporation can be increased significantly.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for the production of poly-β-hydroxybutyrate, comprising:

(a) introducing into a prokanyotic host cell capable of metabolizing sucrose a vector construct which directs the expression of a sequence which encodes a poly-β-hydroxybutyrate biosynthetic pathway, said prokaryotic host cell selected from the group consisting of *E. coli* and Klebsiella;

(b) culturing said host cell in medium containing sucrose; and (c) isolating poly-β-hydroxybutyrate from said cultured host cell.

2. A method for the production of poly-β-hydroxyalkanoate copolymer, comprising:

(a) introducing into a prokaryotic host cell capable of metabolizing sucrose and expressing acetate utilization enzymes constitutively, a vector construct which directs the expression of a sequence which encodes a poly-β-hydroxybutyrate biosynthetic pathway, said prokaryotic host cell selected from the group consisting of *E. coli* and Klebsiella;

(b) culturing said host cell in medium containing propionate or a derivative thereof, and sucrose; and (c) isolating said poly-β-hydroxyalkanoate copolymer from said cultured host cell.

3. The method of claim 1 or 2 wherein said host cell is *E. coli*.

4. The method of claim 1 or 2 wherein said host cell is Klebsiella.

5. The method of claim 4 wherein said host cell is *Klebsiella aerogenes*.

6. The method of claims 1 or 2 wherein said medium contains sucrose as the principal carbon source.

7. The method of claims 1 or 2 wherein said medium comprises molasses.

8. *E. coli* capable of metabolizing sucrose and containing a vector construct which directs the expression of a sequence which encodes a biosynthetic pathway of poly-β-hydroxybutyrate.

9. Klebsiella capable of metabolizing sucrose and containing a vector construct which directs the expression of a sequence which encodes a biosynthetic pathway of poly-β-hydroxybutyrate.

10. A method for the production of poly-β-hydroxybutyrate, comprising:

(a) introducing into a Klebsiella host cell capable of metabolizing sucrose, a vector construct which directs the expression of a sequence which encodes a poly-β-hydroxybutyrate biosynthetic pathway;

(b) culturing said host cell in medium containing sucrose; and (c) isolating poly-β-hydroxybutyrate from said cultured host cell.

11. A method for the production of poly-β-hydroxyalkanoate copolymer, comprising:

(a) introducing into a Klebsiella host cell capable of metabolizing sucrose and expressing acetate utilization enzymes constitutively, a vector construct which directs the expression of a sequence which encodes a poly-β-hydroxybutyrate biosynthetic pathway;

(b) culturing said host cell in medium containing propionate or a derivative thereof, and sucrose; and (c) isolating said poly-β-hydroxyalkanoate copolymer from said cultured host cell.

12. The method of claim 4 wherein said host cell is *Klebsiella oxytoca*.

13. The method of claim 10 or 11 wherein said host cell is *Klebsiella aerogenes*.

14. The method of claim 10 or 11 wherein said host cell is *Klebsiella oxytoca*.

15. The method of claim 4 wherein said host cell is *Klebsiella oxytoca*.

16. The Klebsiella of claim 9 wherein said Klebsiella is *Klebsiella aerogenes*.

17. The Klebsiella of claim 9 wherein said Klebsiella is *Klebsiella oxytoca*.

* * * * *

UNITED STATES PATENT AND TRADEMARK OFFICE
CERTIFICATE OF CORRECTION

PATENT NO.    : 5,569,595
DATED         : October 29, 1996
INVENTOR(S)   : Douglas E. Dennis and Steven C. Slater It is certified that error appears in the above identified patent and that said Letters Patent is hereby corrected as shown below:

On the title page in Field [75] denoting the inventors, please add --Steven C. Slater, Cambridge, Ma.--

In column 18, claim 1, line 13, please delete "prokanyotic" and insert therefor --prokaryotic--.

Signed and Sealed this

Twelfth Day of August, 1997

*Attest:*

BRUCE LEHMAN

*Attesting Officer*    Commissioner of Patents and Trademarks